(12) United States Patent
Sterrett et al.

(10) Patent No.: US 10,966,660 B2
(45) Date of Patent: Apr. 6, 2021

(54) INTEGRATED SENSORS FOR MEDICAL DEVICES AND METHOD OF MAKING INTEGRATED SENSORS FOR MEDICAL DEVICES

(71) Applicant: St. Jude Medical International Holding S.à r.l., Luxembourg (LU)

(72) Inventors: Terry Sterrett, Huntington Beach, CA (US); Allyn Jensrud, Burnsville, MN (US)

(73) Assignee: St. Jude Medical International Holding S.à r.l., Luxembourg (LU)

( * ) Notice: Subject to any disclaimer, the term of this patent is extended or adjusted under 35 U.S.C. 154(b) by 0 days.

(21) Appl. No.: 16/795,073

(22) Filed: Feb. 19, 2020

(65) Prior Publication Data
US 2020/0196952 A1    Jun. 25, 2020

Related U.S. Application Data

(63) Continuation of application No. 15/146,564, filed on May 4, 2016, now Pat. No. 10,602,983.

(60) Provisional application No. 62/158,795, filed on May 8, 2015.

(51) Int. Cl.
| | | |
|---|---|---|
| *A61B 5/00* | (2006.01) | |
| *A61B 5/042* | (2006.01) | |
| *A61B 18/14* | (2006.01) | |
| *C25D 5/56* | (2006.01) | |
| *C25D 5/02* | (2006.01) | |
| *A61B 34/20* | (2016.01) | |

(52) U.S. Cl.
CPC .......... *A61B 5/6852* (2013.01); *A61B 5/0422* (2013.01); *A61B 18/1492* (2013.01); *C25D 5/022* (2013.01); *C25D 5/56* (2013.01); *A61B 2034/2051* (2016.02); *A61B 2562/04* (2013.01); *A61B 2562/06* (2013.01); *A61B 2562/125* (2013.01)

(58) Field of Classification Search
None
See application file for complete search history.

(56) References Cited

U.S. PATENT DOCUMENTS

| 4,564,744 A | 1/1986 | Valentin |
| 6,059,779 A | 5/2000 | Mills |

(Continued)

*Primary Examiner* — Cachet I Proctor
(74) *Attorney, Agent, or Firm* — Dykema Gossett PLLC

(57) ABSTRACT

A sensor for a medical device including a plurality of sensor segments. Each of the plurality of sensor segments can include a layer of magnetically-permeable material and a layer of electrically-conductive material disposed on the layer of magnetically-permeable material. In an example, the layer of magnetically-permeable material can be arranged in a partially-annular shape. The sensor segments can include an electrical connection formation that extends transverse to the layers of magnetically-permeable material and electrically-conductive material. The electrical connection formation can be electrically coupled with the layer of electrically-conductive material. The plurality of sensor segments can be electrically coupled with each other through an electrical coupling of the respective layer of electrically-conductive material of each sensor segment with the electrical connection formation of another sensor segment.

19 Claims, 17 Drawing Sheets

(56) References Cited

U.S. PATENT DOCUMENTS

| | | | |
|---|---|---|---|
| 6,223,085 B1* | 4/2001 | Dann | A61B 18/1492 |
| | | | 606/29 |
| 7,262,680 B2* | 8/2007 | Wang | H01F 17/0013 |
| | | | 257/531 |
| 8,187,267 B2 | 5/2012 | Pappone et al. | |
| 8,517,999 B2 | 8/2013 | Pappone et al. | |
| 9,101,046 B2 | 8/2015 | Sobe | |
| 9,179,971 B2* | 11/2015 | Kirschenman | A61B 5/0422 |
| 2001/0056280 A1 | 12/2001 | Underwood et al. | |
| 2005/0261543 A1* | 11/2005 | Abe | A61M 1/122 |
| | | | 600/16 |
| 2010/0191232 A1 | 7/2010 | Boveda | |
| 2011/0178594 A1* | 7/2011 | Kim, II | A61L 31/041 |
| | | | 623/1.44 |
| 2011/0195104 A1* | 8/2011 | Jiang | A61Q 19/00 |
| | | | 424/405 |
| 2011/0233820 A1 | 9/2011 | Watanabe et al. | |
| 2011/0313237 A1* | 12/2011 | Miyakoshi | A61M 1/3659 |
| | | | 600/16 |
| 2012/0029504 A1 | 2/2012 | Alfonso et al. | |
| 2012/0071870 A1 | 3/2012 | Salahieh et al. | |
| 2012/0172842 A1 | 7/2012 | Sela et al. | |
| 2014/0132904 A1* | 5/2014 | Bos | G02F 1/134309 |
| | | | 349/139 |
| 2014/0276788 A1* | 9/2014 | Nguyen | A61B 18/1492 |
| | | | 606/41 |
| 2015/0182282 A1* | 7/2015 | Zemel | A61B 18/042 |
| | | | 606/41 |
| 2016/0121143 A1 | 5/2016 | Mumaw et al. | |
| 2016/0320210 A1* | 11/2016 | Nelson | A61B 5/062 |

* cited by examiner

INTEGRATED SENSORS FOR MEDICAL DEVICES AND METHOD OF MAKING INTEGRATED SENSORS FOR MEDICAL DEVICES

CROSS-REFERENCE TO RELATED APPLICATIONS

This application is a division of U.S. application Ser. No. 15/146,564, filed 4 May 2016 (the '564 application), now pending, which claims the benefit of U.S. provisional application No. 62/158,795, filed 8 May 2015 (the '795 application). The '564 application and the '795 application are both hereby incorporated by reference as though fully set forth herein.

BACKGROUND a. Technical Field

The instant disclosure relates to the design, manufacture, and assembly of sensors for medical devices, including sensors manufactured according to semiconductor fabrication techniques.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site such as, for example, a site within the patient's heart. The catheter typically carries one or more sensors which may be used for a variety of purposes including application of ablation energy, position sensing, collecting electrophysiological data, detecting the temperature or other characteristics of tissue, and the like. Such sensors may be disposed on either the interior or exterior of the catheter.

Sensors are typically assembled onto or into the catheter during the manufacture of the shaft or assembly of the catheter. For example, a sensor may be incorporated into the shaft by placing it between layers of a melt-processing polymer and then reflowing the polymer to encapsulate the sensor. In another example, an electrode may be placed on the exterior of the shaft during assembly of the catheter.

The foregoing discussion is intended only to illustrate the present field and should not be taken as a disavowal of claim scope.

BRIEF SUMMARY

An exemplary embodiment of a first method of manufacturing a sensor for a medical device may comprise providing a tip electrode comprising an atraumatic distal tip portion and a tubular proximal portion and depositing a layer of dielectric material around a longitudinal axis. The first method may further comprise depositing a first layer of electrically-conductive material radially outward of the layer of dielectric material to form a plurality of electrically-conductive annular portions, and depositing a second layer of electrically-conductive material to electrically couple adjacent ones of the plurality of electrically-conductive annular portions.

An exemplary embodiment of a second method of manufacturing a sensor for a medical device may comprise providing a plurality of sensor segments. Providing each one of the plurality of sensor segments may comprise providing a sheet of magnetically-permeable material, plating a layer of electrically-conductive material in a partially-annular shape on a surface of the sheet of magnetically-permeable material, and forming an electrical connection formation that extends transverse to the surface of the sheet, wherein the electrical connection formation is electrically coupled with the layer of electrically-conductive material. The second method may further comprise electrically coupling the plurality of sensor segments with each other by electrically coupling the respective layer of electrically-conductive material of each sensor segment with the electrical connection formation of another sensor segment.

An exemplary embodiment of a third method of manufacturing a sensor for a medical device may comprise forming a channel in a substrate, depositing a dielectric material in the channel, depositing an electrically-conductive material in the channel so as to form a coil of electrically-conductive material that defines a longitudinal axis, and depositing a magnetically-permeable material in the channel so as to form a core in the coil, the core extending along the axis.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

Figure 1:
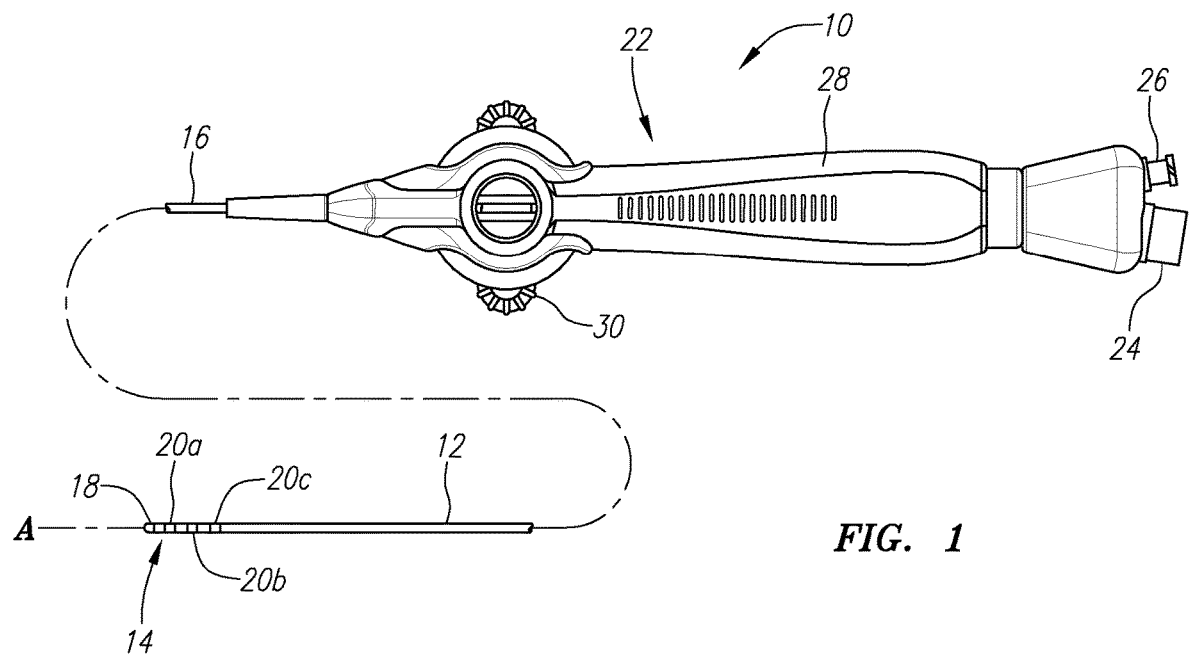
FIG. 1 is a plan view of an exemplary elongate medical device.

Referring now to the figures, in which like numerals indicate the same or similar elements in the various views, FIG. 1 is a plan view of an exemplary elongate medical device 10. The elongate medical device 10 may be a catheter, introducer, or other elongate medical device type. The elongate medical device 10 will be referred to herein as a catheter for ease of description (i.e., catheter 10). It should be understood, though, that the elongate medical device is not limited to a catheter.

The catheter 10 may include an elongate tubular shaft 12 defining a longitudinal axis A and having a distal end portion 14 and a proximal end portion 16, an atraumatic tip electrode 18, a number of ring electrodes 20a, 20b, 20c (which may be referred to collectively as the ring electrodes 20 or individually as a ring electrode 20), and a handle 22 coupled with the catheter shaft 12. The handle 22 may include one or more electromechanical connectors 24 configured to allow the catheter 10, and the electrodes 18, 20 thereof, in particular, to be coupled with components or subsystems of, for example, an electrophysiology (EP) laboratory system. Such components or subsystems may comprise, for example and without limitation, a visualization, navigation, and/or mapping system, an EP monitoring and recording system (e.g., for monitoring and/or recording electrocardiograms (EGM), cardiac signals, etc.), a tissue contact sensing system, an ablation system, a cardiac stimulation system (i.e., EP stimulator), and the like. An exemplary system is shown in U.S. patent application publication no. 2012/0029504, which is hereby incorporated by reference in its entirety as though fully set forth herein.

The catheter 10 may further comprise one or more fluid connectors 26 configured to provide the catheter 10, and particularly the shaft 12, with connectivity between one or more fluid lumen(s) in the shaft 12 and external systems. The fluid connector 25 may thus be fluidly coupled with one or more fluid lumens in the shaft 12 and/or handle 22 and may be configured for connection with a source or destination of such fluids such as, for example only, a gravity feed or pump for irrigation fluids.

In addition to and/or instead of one or more electrodes 18, 20, the catheter 10 may be equipped with one or more additional types of sensors. For example, the catheter 10 may be equipped with one or more coil sensors, temperature sensors, pressure sensors, and/or other sensors. Additionally, some or all of the steps, methods, and procedures described and/or illustrated herein related to the manufacturing, assembly, and use of electrodes 18, 20 on the catheter 10 may also apply to other types of sensors disposed on or in the catheter 10.

The handle 22 may be disposed at the proximal end portion 16 of the shaft 12. The handle 22 may provide a location for a clinician to hold the catheter 10 and may further provide means for steering or guiding the shaft 12 within the body of a patient.

The handle 22 may comprise a housing 28. The housing 28 may be of a unitary construction or may be constructed of a plurality of pieces that are configured to be assembled together. In a multi-piece embodiment, the housing 28 may be coupled together in any number of ways known in the art, such as, for example, by press fit or interference coupling techniques, by complementary interlocking members, by conventional fasteners or adhesives, or any other techniques known in the art.

Within the housing 28, one or more wires may be provided to electrically couple the electromechanical connector 24 with the electrical infrastructure of the shaft 12. For example, in an embodiment, one wire may be provided for each electrical trace on a surface of the shaft, as shown and described in detail below. A wire in the housing 26 may be soldered to an electrical trace and/or contact pad on one end, for example, and soldered or otherwise electrically coupled to the electromechanical connector 24 within the housing 28 on the other end.

In an exemplary embodiment, the catheter 10 may further comprise a deflection mechanism 30 associated with the handle 22 of the catheter 10. The deflection mechanism 30 may be coupled with a pull assembly (not shown) disposed at or in the distal end portion 14 of the shaft 12. The combination of the deflection mechanism 30 and the pull assembly provides a means by which a user or physician can effect movement (e.g., deflection) of the distal end portion 14 in one or more directions, and therefore, allows the physician to steer the catheter shaft 12.

Figure 2:
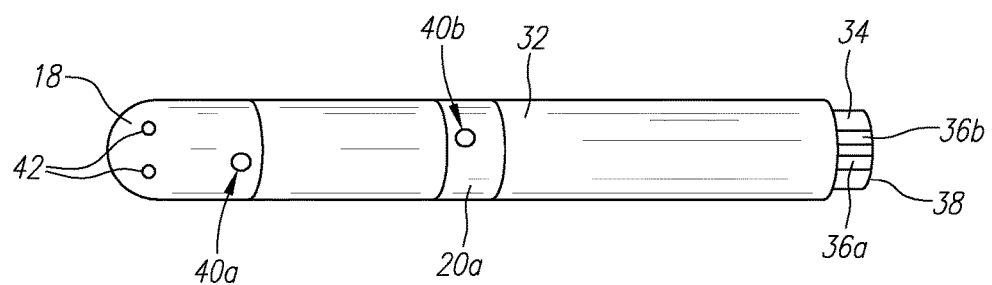
FIG. 2 is an isometric view of an exemplary embodiment of a distal end portion of an elongate medical device.

FIG. 2 is an isometric view of an embodiment of the distal end portion 14 of the catheter 10, with a portion of an outer tube 32 of the shaft 12 cut away to expose an inner tube 34. The inner tube 34 may extend within the outer tube 32, and a first electrically-conductive trace 36a and a second electrically-conductive trace 36b may be disposed on an outer surface 38 of the inner tube 34. The distal end portion 14 may include, as noted above, a tip electrode 18 and one or more ring electrodes 20 (one such ring electrode 20a is shown in FIG. 2). The tip electrode 18 may define a first bore 40a (i.e., via), and the ring electrode may define a second bore 40b (i.e., via). Vias 38a and 38b may be referred to collectively as the bores 40 or individually as the bore 40. Each bore 40 may extend, substantially orthogonal to the axis A of the shaft 12, from an exterior surface of the electrode 18, 20 to a portion of a respective one of the traces 36. Thus, the first bore 40a may extend from an exterior surface of the tip electrode 18, through a portion of the body of the electrode 18 to a portion of a first trace 36a, and the second bore 40b may extend from the exterior surface of the ring electrode 20a to a portion of a second trace 36b.

The first bore 40a may be filled with an element (e.g., a material) that electrically couples the tip electrode 18 with the first trace 36a, and the second bore 40b may also be filled with an element (e.g., a material) that electrically couples the band electrode 20a with the second trace 36b. For example, in an embodiment, each bore 40 may be filled with an electrically-conductive adhesive. Such an electrically-conductive adhesive may include, for example only, silver-filled polyurethane, epoxy, and/or silicone adhesive.

The tip electrode 18 may further include one or more irrigation ports 42, in an embodiment. Irrigation fluid may be provided from a system disposed at the proximal end of the catheter (e.g., a gravity feed or pump, as noted above) and may flow through the irrigation ports 39 in order to, for example only, cool the tip electrode. Additional details regarding irrigated electrodes may be found, for example, in U.S. Pat. Nos. 8,517,999 and 8,187,267, both of which are hereby incorporated by reference in their entireties.

In an embodiment, the inner tube 34 may comprise some or all of a fluid lumen for the catheter 10. The fluid lumen may be configured to carry one or more fluids (e.g., irrigation fluid) between the handle of the finished device and the distal tip of the finished device. Fluid may flow through the inner tube 32 to the irrigation ports 42, in an embodiment.

Referring to FIGS. 1 and 2, each of the electrically-conductive traces 36 may extend from the distal end portion 14 of the shaft 12 to the proximal end portion 16 of the shaft 12, in an embodiment. Each trace 36 may extend over substantially the entire length of the shaft 12, in an embodiment. For example, each trace 34 may extend over 90% or more of the length of the catheter shaft 12. In an embodiment, one or more of the traces 36 may include one or more interruptions and/or discontinuities. For example but without limitation, a distal portion of a trace 36 may extend from the distal end portion 14 of the shaft 12, be electrically coupled with a distal end of a flex circuit, such as a flex circuit as illustrated and described in U.S. patent application publication no. 2012/0172842, which is hereby incorporated by reference in its entirety as though fully set forth herein, and a proximal portion of the trace 36 may be electrically coupled with a proximal end of the flex circuit and may continue extending proximally to the proximal end portion 16 of the shaft 12.

FIG. 2 illustrates an example of semiconductor fabrication techniques (i.e., which may be used to manufacture the traces 36 and vias 40) used in the manufacture of a medical device. Such traces and vias may be combined, in embodiments, with sensors manufactured according to semiconductor fabrication techniques (i.e., integrated circuit fabrication techniques). For example, one or more sensors may be manufactured according to integrated circuit fabrication techniques (such sensors are referred to herein as integrated sensors), incorporated into a structure of a medical device, and electrically coupled with an electrically conductive trace similar to the traces 36, in an embodiment. Additionally or alternatively, such a sensor may be electrically coupled with standard wiring, such as a twisted-wire pair, in an embodiment.

Various methods and processes that incorporate semiconductor fabrication techniques may be used, in embodiments, to integrate one or more sensors in one or more components (i.e., structures) of a medical device such as, but not limited to, a medical device such as, but not limited to, a catheter or other elongate medical device, an implantable device (e.g., an implantable retinal prosthesis, implantable medication delivery pump), an injectable device (e.g., an injectable radiofrequency (RF) transmitter or receiver), a pressure measurement device (e.g., a temporary ocular pressure measurement device), etc. For example, methods and processes that incorporate semiconductor fabrication techniques may be applied to integrate one or more sensors into an electrode (e.g., an electrode 18, 20), a portion of the shaft (e.g., a polyimide or other polymer layer of the shaft), and/or other structures of the medical device. Such techniques may be applied, in embodiments, to achieve sensors having features as small as twenty (20) nanometers (nm). The sensors that may be integrated into a medical device according to the present disclosure include, but are not limited to, position sensors (e.g., GPS sensors), strain gauges, other transducers, and the like. FIGS. 3A-12C illustrate various steps in numerous such techniques, and are described below in turn.

FIGS. 3A-3H are diagrammatic side views of various steps in an exemplary embodiment of a first method of manufacturing an integrated sensor for a medical device. FIGS. 4A-4M are diagrammatic top views of various steps of the first method. FIG. 5 is a diagrammatic isometric view of an integrated sensor at a late stage of the first method. FIGS. 3A-4M are illustrated with respect to a coordinate system having X, Y, and Z axes.

The first method will be described with reference to an embodiment in which a coil sensor is manufactured. It should be understood, however, that the first method is not limited to a coil sensor unless explicitly set forth in the claims. Instead, the first method (or variations thereof) may be applied to manufacture a variety of different sensor shapes and configurations.

Figure 3A:
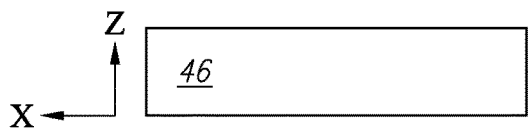
FIGS. 3A-3H are diagrammatic side views of various steps in an exemplary embodiment of a first method of integrating a sensor into a medical device structure.
Figure 4A:
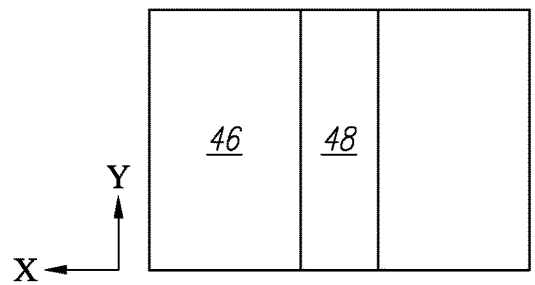
FIGS. 4A-4M are diagrammatic top views of various steps of the method of FIGS. 3A-3H.

Referring to FIG. 3A, the first method may begin with providing a substrate 46. The substrate 46 may be or may include, in an embodiment, a structure intended for inclusion in a completed medical device. In an embodiment, the substrate 46 may be or may include a polymer or a metal. The substrate 46 may be or may include a flex substrate, in an embodiment, comprising polyimide, polyether ether ketone (PEEK), and/or another suitable material.

Figure 3B:
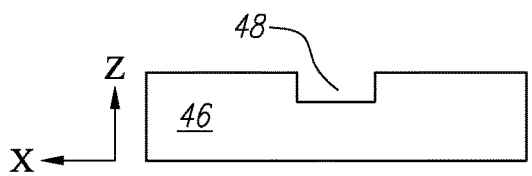

The first method may continue to forming a channel 48 in the substrate. FIGS. 3B and 4A illustrate the channel 48. The channel 48 may be formed by techniques appropriate for the substrate material. The channel 48 may be rectangular in cross-section, in an embodiment. Of course, the channel 48 may have some other shape, in an embodiment. The shape of the channel 48 may be selected according to the desired shape and configuration of the sensor to be manufactured.

Figure 4B:
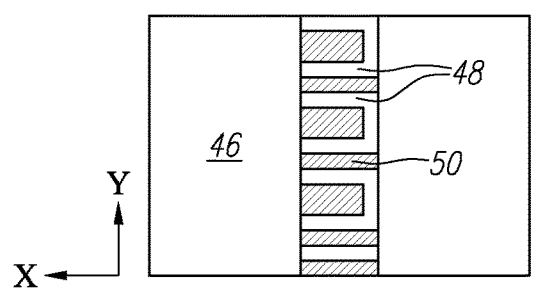
Figure 3C:
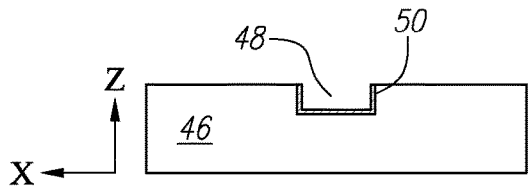
Figure 3D:
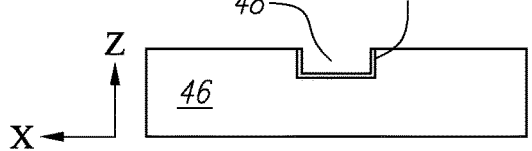
Figure 5:
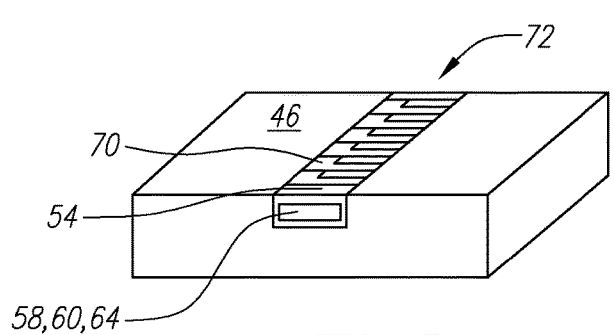
FIG. 5 is a diagrammatic isometric view of an integrated sensor at a late stage of the method of FIGS. 3A-3H and 4A-4M.

As shown in FIGS. 3C and 4B, the method may further include applying a dielectric material 50 in the channel in a desired pattern. Applying the dielectric material 50 may include depositing a layer of dielectric material 50 in the channel 48 and patterning the deposited dielectric material 50, in an embodiment. Patterning the dielectric material 50 may include masking the channel 48 with a first mask layer, and developing the dielectric material 50 to remove the non-masked portions of the dielectric material 50. Accordingly, the mask may be placed over the layer of dielectric material to reveal the pattern desired for the dielectric material 50.

As used herein, "depositing" materials is used to refer generally to any and all methods of transferring the subject material onto the assembly. For example, a "depositing" step in a method of this disclosure may include one or more of physical vapor deposition (PVD), chemical vapor deposition (CVD), electrochemical deposition (ECD), molecular beam epitaxy (MBE), atomic layer deposition (ALD), and any other deposition technique. Furthermore, as used herein, "applying" may be a generic term for transferring a material onto an assembly; as noted above, applying may include depositing, patterning, and/or other processes, depending on the material applied, the assembly to which it is applied, and the context in which the application is described.

Various processes typically found in semiconductor or integrated circuit fabrication, such as deposition, patterning, masking, etching, developing, etc., are generally referred to herein. It should be understood that those processes may include a number of respective substeps and variations, which substeps and variations are not described herein. Such substeps and variations are within the scope of the knowledge of a person of skill in the art, however, and thus may be omitted from the explicit description herein. But such substeps and variations are contemplated and within the scope of the instant application. For example, as noted below, one or more of the sensors of this disclosure may be fabricated according to complementary metal-oxide-semiconductor (CMOS) techniques, and thus may include processes such as deposition of photoresist, exposing photoresist, and etching photoresist in the course of providing a mask for an electrically-conductive material. This and other processes in CMOS and other semiconductor fabrication techniques are known in the art and are discussed in a simplified manner in this disclosure for ease of description.

A first layer of electrically-conductive material may be applied onto the portions of the channel not covered by the dielectric material, in an embodiment. This application is described below with reference to a seeding and plating process, but the first method is not so limited except as explicitly recited in the claims. Rather, additional or alternative material application processes may be applied, in an embodiment.

Figure 4C:
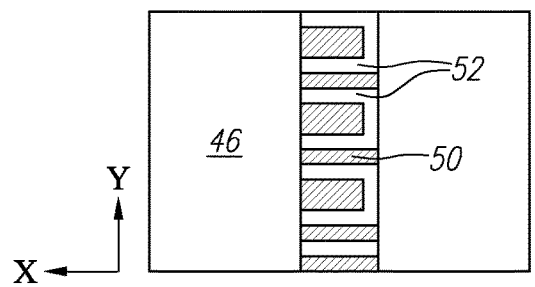
Figure 4D:
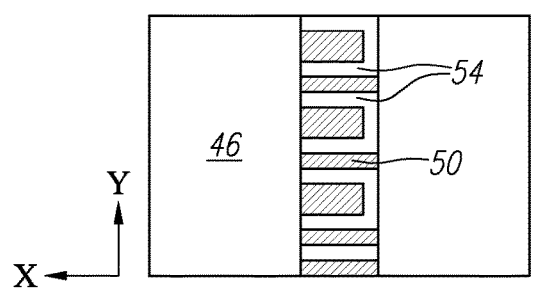
Figure 3E:
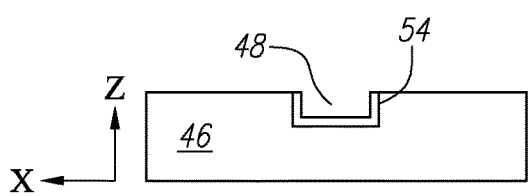

The first layer of electrically-conductive material may include two sub-layers, in an embodiment. First, a mask may be placed over the dielectric material, and a first sub-layer 52—i.e., a seed layer 52—of electrically-conductive material may be deposited in the non-masked areas of the channel 48. Without the mask, the assembly of FIGS. 3D and 4C may result. Then, as shown in FIGS. 3E and 4D, a second sub-layer of electrically-conductive material may be electroplated on the seed layer 52 to create a unitary first layer 54 of electrically-conductive material. The seed sub-layer 52 and the electroplated sub-layer may comprise the same material composition, in an embodiment. The electrically-conductive material 52, 54 may be or may include copper, in an embodiment.

Figure 3F:
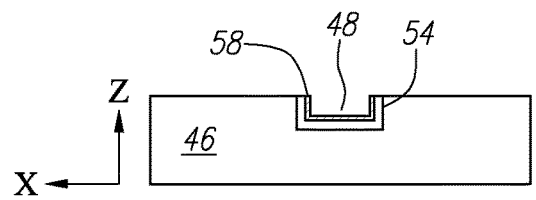
Figure 4E:
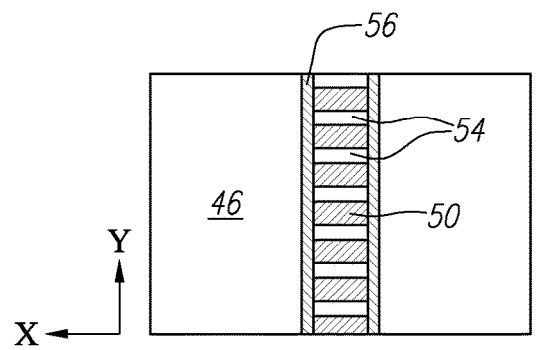
Figure 4F:
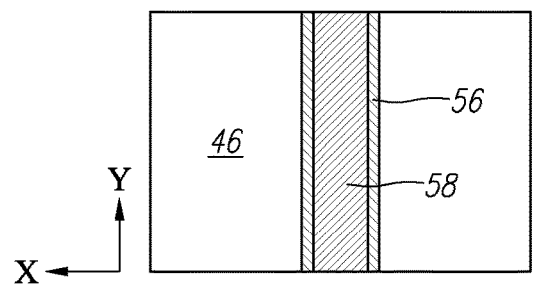

Following application of the electrically-conductive material 52, 54, a layer of magnetically-permeable material may be applied, in an embodiment, which may be separated from the electrically-conductive layer by dielectric material. For example, as shown in FIG. 4E, a mask layer 56 may be placed over portions of the first dielectric layer 50 and the first electrically-conductive layer 54. On top of the mask layer 56, as shown in FIGS. 3F and 4F, a second dielectric layer 58 may be deposited and patterned. In an embodiment, following deposition and patterning, the second dielectric layer 58 may cover a portion of the first electrically-conductive layer 54, as shown in FIG. 3F. The second dielectric layer 58 may also cover non-masked portions of the first dielectric layer 50, in an embodiment.

Figure 3G:
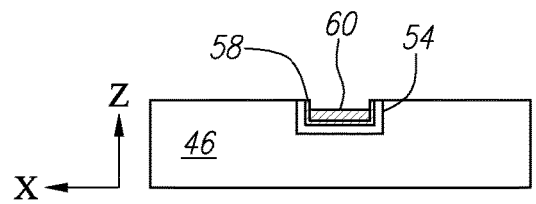
Figure 4G:
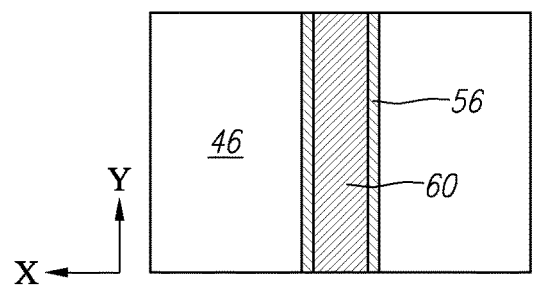

Referring to FIGS. 3G and 4G, a layer of magnetically-permeable material 60 may be deposited over the second dielectric layer 58. The magnetically-permeable material 60 may form a core for a coil sensor in the completed integrated sensor, in an embodiment. Accordingly, the magnetically permeable material 60 may be or may include a material of sufficient magnetic permeability for the completed coil sensor to be capable of having an electrical signal induced by a magnetic field, and/or to produce a magnetic field according to an electrical signal driven through the sensor. In an embodiment, the magnetically-permeable material 60 may be or may include mu-metal.

In an embodiment, the magnetic permeability of the magnetically-permeable material 60 may be selected (that is, the type and composition of the material) may be selected according to the design requirements of the sensor. In an embodiment, the magnetic permeability of the magnetically-permeable material 60 may be one hundred (100) H/m or greater. Still further, in an embodiment, the magnetic permeability of the magnetically-permeable material 60 may be five hundred (500) to two hundred thousand (200,000) H/m or more. Still further, in an embodiment, the magnetic permeability of the magnetically-permeable material 60 may be two thousand (2,000) H/m or more.

Figure 4H:
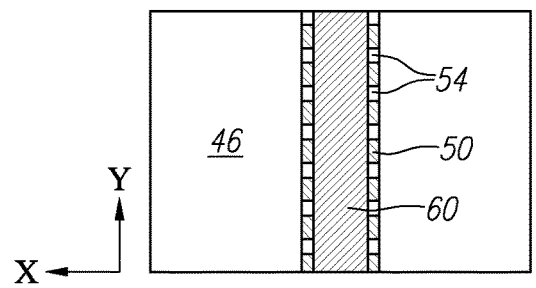
Figure 4I:
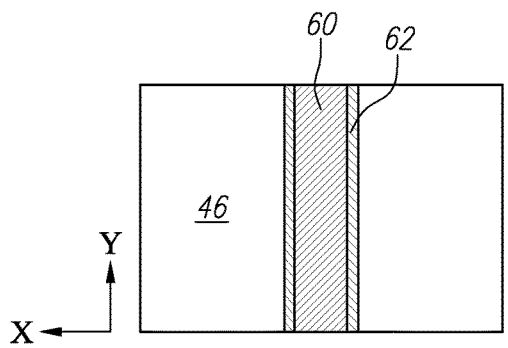

Following application of the layer of magnetically-permeable material 60, the mask layer 56 may be removed (e.g., stripped). FIG. 4H illustrates the assembly following mask stripping. As shown in FIG. 4I, a further mask layer 62 may be placed so as to expose the "top" (i.e., along the Z-axis) of the magnetically-permeable layer 60, and a second layer 64 of dielectric material may be deposited and patterned to cover the non-masked area. The mask 62 may be stripped, resulting in the assembly illustrated in FIG. 4J.

Figure 3H:
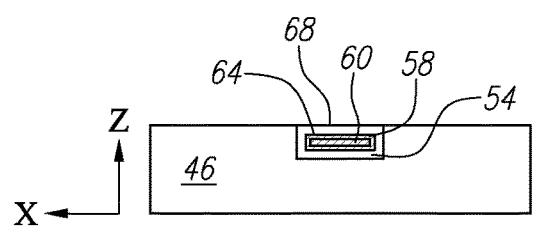
Figure 4L:
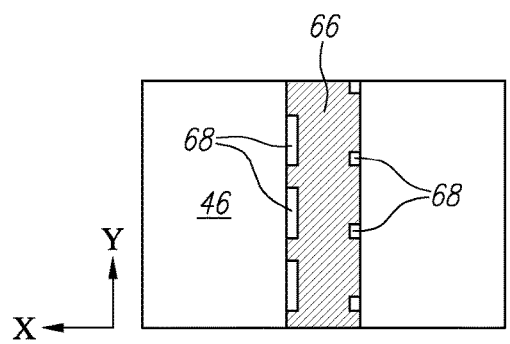
Figure 4J:
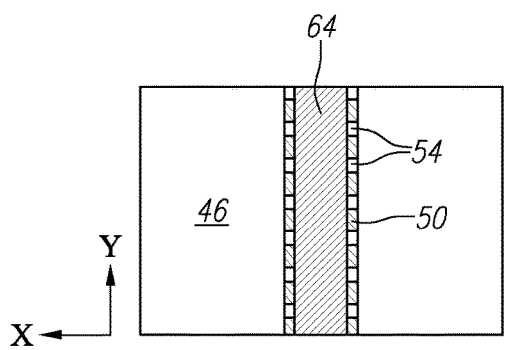
Figure 4M:
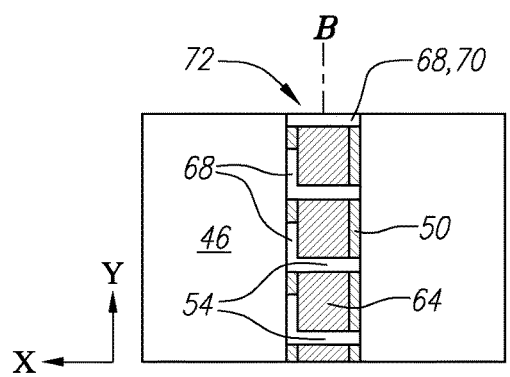
Figure 4K:
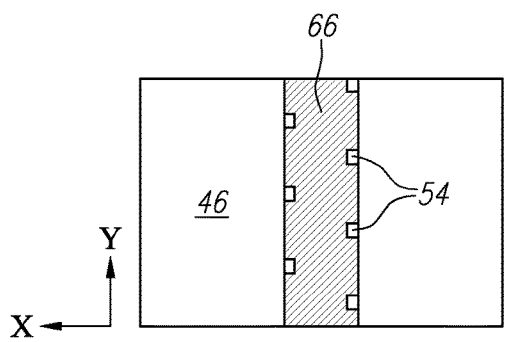

Two further iterations of applying electrically-conductive material may be performed, each iteration resulting in the application of a portion of a second layer of electrically-conductive material. As before, applying the layer of electrically-conductive material may include masking, seeding, and electroplating, in an embodiment. The second layer of electrically-conductive material may be the same material or materials as the first layer of electrically-conductive material, in an embodiment. A first iteration of applying may provide electrical connections between segments of electrically-conductive material along the X-axis; a second iteration of applying may provide electrical connections between segments of electrically-conductive material along the Y-axis. FIG. 4K illustrates the mask 66 used for the second iteration, and FIG. 4L illustrates the assembly following seeding and electroplating the second iteration, including the second layer 68 of electrically-conductive material. As illustrated in FIGS. 4M and 3H, after applying the second layer 68 of electrically-conductive material, the remaining mask may be removed (e.g., stripped) to reveal a daisy-chained electrical connection of all segments of electrically-conductive material to form a coil 70 in a sensor 72.

FIG. 5 also illustrates the sensor 72 of FIG. 4M, with the magnetically-permeable material 60 and the first and second layers of dielectric material 58, 64 consolidated for clarity of illustration. As shown in FIGS. 4M and 5, the electrically conductive material may form a continuous coil 70 that defines an axis B along the Y-axis. The axis B may extend through the magnetically-permeable layer 60, in an embodiment. The coil 70 may comprise a plurality of partially-annular portions which may comprise, in an embodiment, the first layer of electrically-conductive material 54. Instead of or in addition to partially-annular portions, the coil 70 may comprise a plurality of horseshoe-shaped portions, bracket-shaped portions, or some other shaped portions. The partially-annular portions may be separated along the axis B by the portions of dielectric material 58, 64, in an embodiment. The magnetically-permeable material 60 may form a core at the radial center (relative to the axis B) of each partially-annular portion. Axially-adjacent (again, with respect to axis B) partially-annular portions may be electrically coupled with each other with axially-extending and/or radially-extending (relative to axis B) electrically-conductive portions which may comprise, in an embodiment, the second electrically-conductive layer 68.

The sensor 72 of FIG. 5 may be incorporated into a medical device in one of several ways. For example, as noted above, the substrate 46 may be a flex substrate. Such a flex substrate may be applied to a portion of a catheter shaft, for example only. Alternatively, the substrate 46 may be a portion of a catheter shaft (e.g., an inner or outer tube of the shaft), an electrode, or some other component of a finished elongate medical device or other medical device.

FIGS. 6A-6I are diagrammatic cross-sectional views of various steps in an exemplary embodiment of a second method of integrating a sensor into a medical device structure. FIGS. 6J-6L are diagrammatic isometric views of various steps of the method.

Figure 6A:
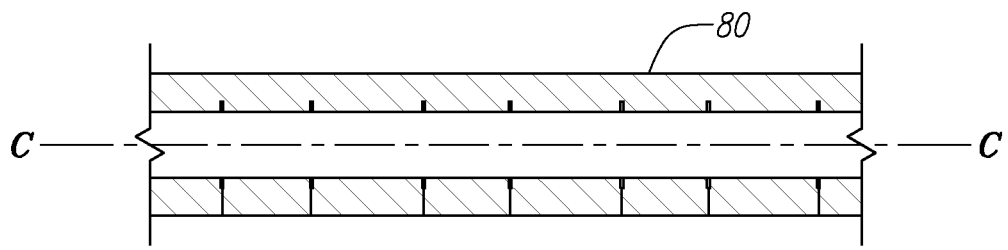
FIGS. 6A-6I are diagrammatic cross-sectional views of various steps in an exemplary embodiment of a second method of integrating a sensor into a medical device structure.
Figure 6B:
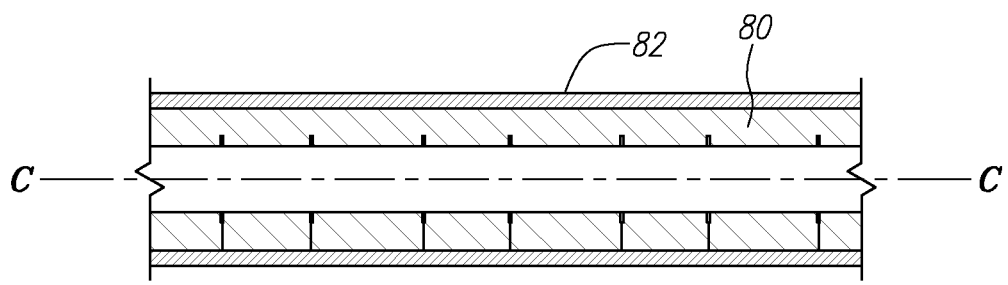

Referring to FIG. 6A, the second method may begin with providing a mandrel 80 defining a longitudinal axis C. Referring to FIG. 6B, a layer of dielectric material 82 may be deposited onto the mandrel 80. Because, in the illustrated embodiment, the sensor is manufactured on a circular mandrel 80, references in the second method to "depositing" materials and other operations should be understood to be with reference to the entire circumference of the assembly, unless otherwise stated. Of course, this arrangement—manufacturing on a circular mandrel 80—is exemplary in nature only.

Figure 6C:
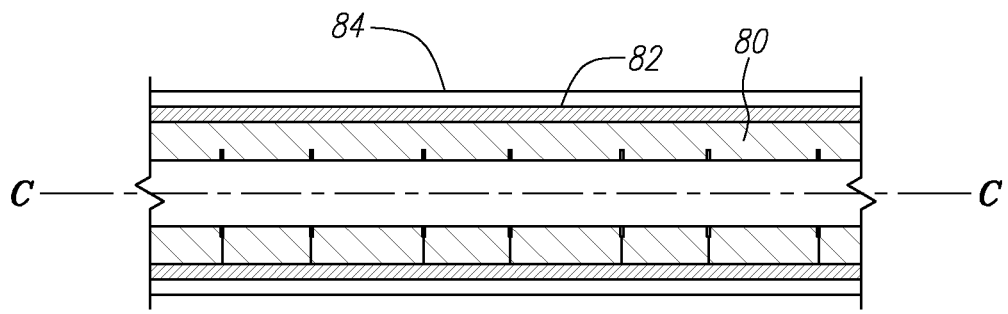

As shown in FIG. 6C, a layer of magnetically-permeable material 84 may be deposited on the dielectric layer 82. The magnetically-permeable material 84 may be or may include mu-metal, in an embodiment.

Figure 6D:
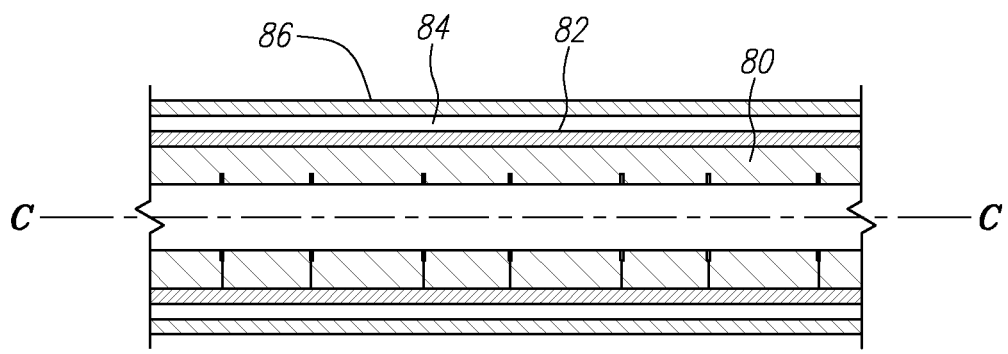
Figure 6E:
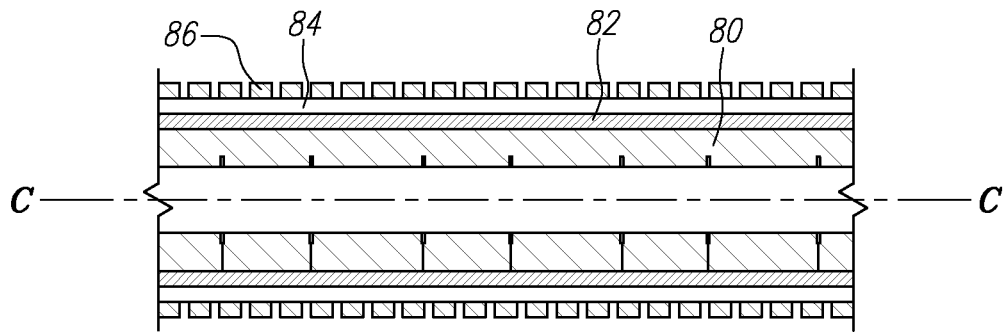

A first mask layer 86 may be applied over the magnetically-permeable layer 84, in an embodiment, as shown in FIG. 6D. The mask layer 86 may be patterned and developed to reveal a desired pattern, as illustrated in FIG. 6E. The pattern may include a plurality of separate rings adjacent a plurality of annular channels, in an embodiment. Alternatively or additionally, the pattern may include a plurality of rings connected by portions of axially-extending material, in an embodiment.

Figure 6F:
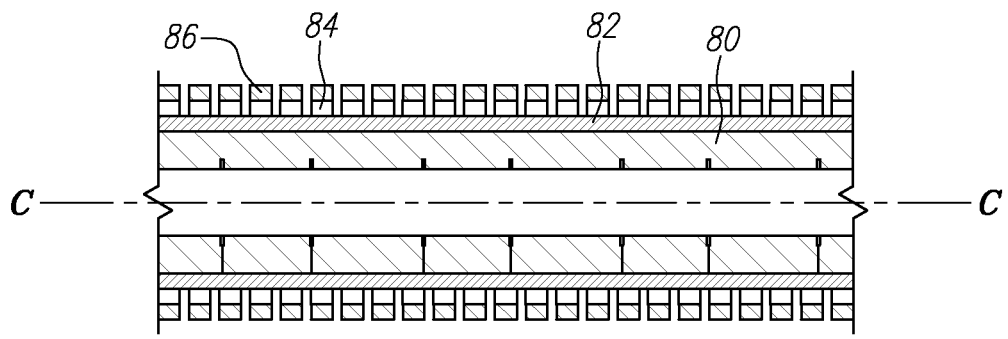

The second method may further include etching the magnetically-permeable layer 84, in an embodiment, according to the pattern defined by the mask layer 86. The patterned magnetically-permeable layer 84, after etching, is shown in FIG. 6F. As illustrated, the magnetically-permeable layer 84 may comprise a plurality of annular portions. Each annular portion may comprise a complete ring (i.e., having a complete continuous circumference), in an embodiment. As noted above, adjacent annular portions may be connected by axially-extending pieces of material, in an embodiment.

Figure 6G:
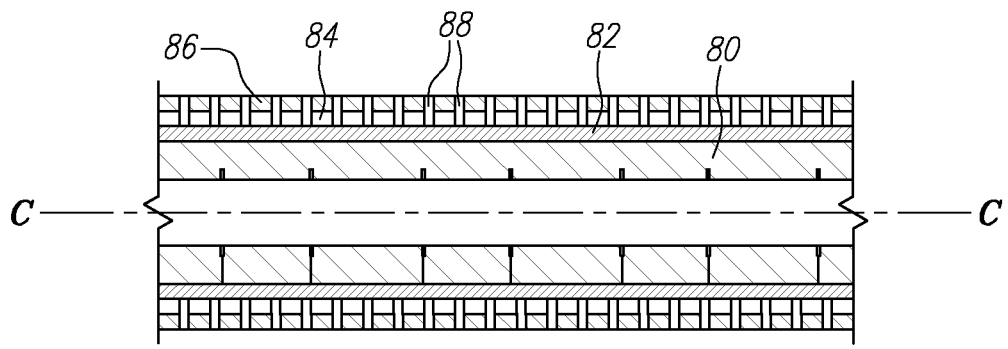

After etching the magnetically-permeable layer 84, both the magnetically-permeable layer 84 and the first mask layer 86 may have the same pattern, in an embodiment. An electrically-conductive material 88 may be applied to fill that pattern, in an embodiment, as shown in FIG. 6G. For example, a seed layer of an electrically-conductive material may be deposited in the non-masked areas, and a layer of electrically-conductive material may be electroplated on the seed layer. The electrically-conductive material 88 may be or may include copper, in an embodiment.

Following the application of the electrically-conductive material 88, the assembly may comprise a plurality of annular electrically-conductive portions separated by annular magnetically-permeable portions and/or annular mask portions, in an embodiment. As noted above, because adjacent ones of the annular magnetically-permeable portions and/or adjacent ones of the mask portions may be connected by axially-extending material, the electrically-conductive annular portions may not form complete rings, in an embodiment. Instead, the annular electrically-conductive portions may extend around less than all of the circumference. Such a shape is referred to herein as "partially annular." For example, in an embodiment, a partially-annular electrically-conductive portion may extend around more than half of the circumference, but less than the entire circumference.

Figure 6H:
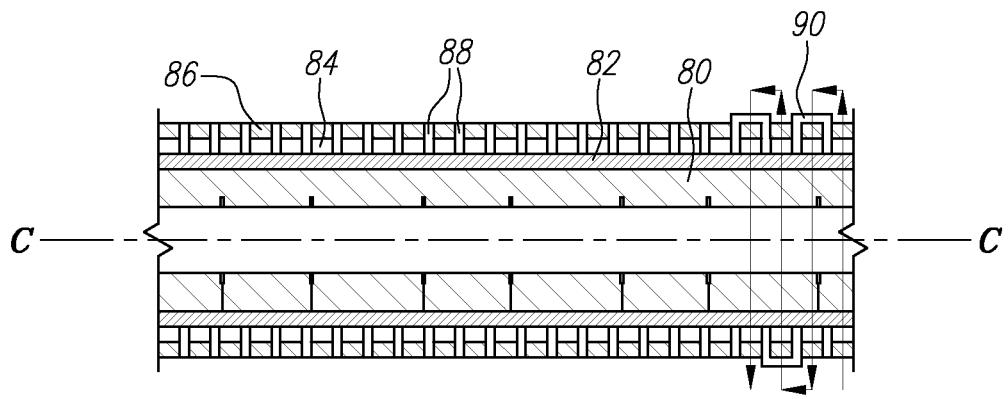
Figure 6I:
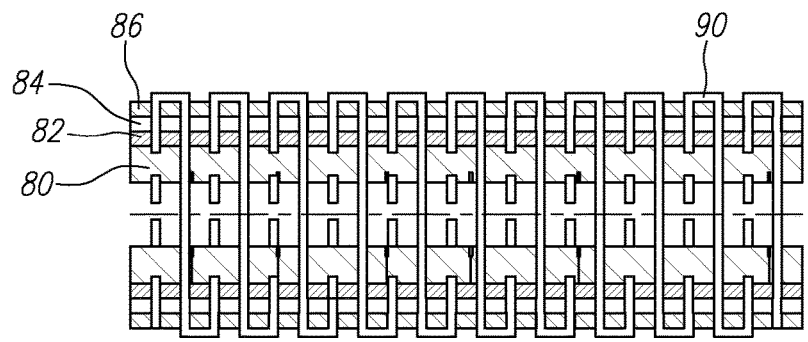
Figure 6J:
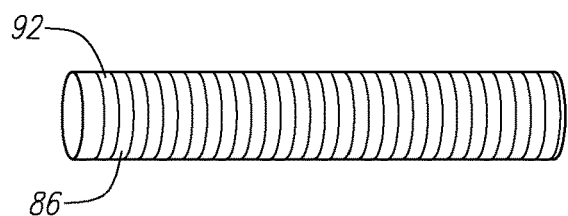
FIGS. 6J-6L are diagrammatic isometric views of various steps in the method of FIGS. 6A-6I.
Figure 6K:
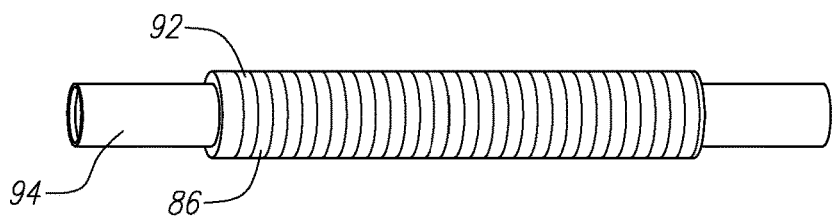
Figure 6L:
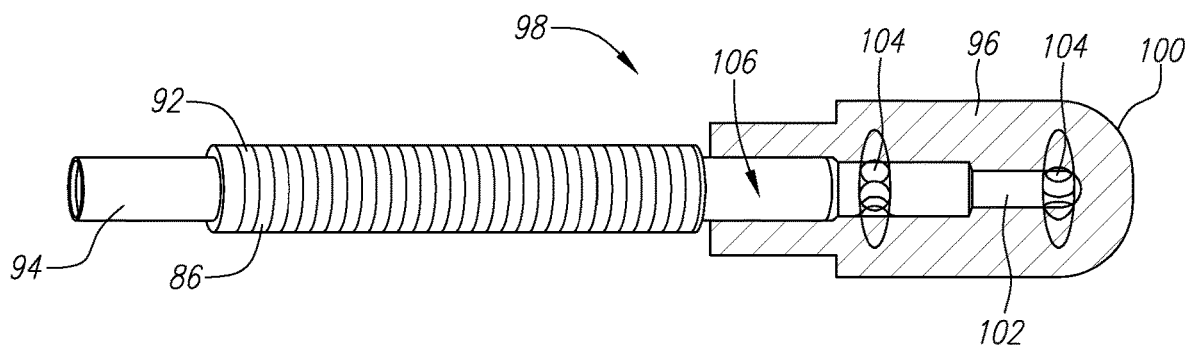

The electrically-conductive annular portions (which, as noted above, may each be partially annular) may be joined by applying a second layer 90 of electrically-conductive material, in an embodiment. FIG. 6H illustrates the assembly after application of a portion of the second layer of electrically-conductive material 90. The second layer of electrically-conductive material 90 may be applied so as to daisy-chain adjacent annular portions together so as to form a continuous coil 92, in an embodiment. FIG. 6I illustrates this continuous coil 92, with portions of the coil 92 that are hidden from view by the remainder of the assembly shown in phantom. The mask 86 may be stripped, in an embodiment. In another embodiment, the mask 86 may be retained, as shown.

The completed coil 92 (along with, in an embodiment, the dielectric layer 82 and magnetically-permeable material layer 84) may be separated from the mandrel, as shown in FIG. 6J, and placed over a structure of a medical device. For example the completed coil assembly may be coupled with a portion of a tip electrode assembly, such as a proximal portion 94 of a tip electrode assembly in an embodiment, as shown in FIG. 6L, which may be coupled with the tip portion 96 of the tip electrode assembly 98, as shown in FIG. 6L. The tip electrode assembly 98 may comprise a distal tip portion 96 and a proximal portion 94, in an embodiment. The distal tip portion 96 may include an atraumatic rounded tip 100, a longitudinal fluid lumen 102, and one or more radially-extending fluid passageways 104 extending from the longitudinal fluid lumen 102 to the exterior of the tip portion 96. A longitudinal lumen 106 defined by the proximal portion 94 may be in fluid communication with the longitudinal lumen 102 of the distal tip portion 96 to, e.g., provide irrigation fluid to the exterior of the distal tip portion 96. The proximal portion 94 may be coupled with the distal tip portion 96 with a biocompatible adhesive, in an embodiment, and/or another mechanical coupling means. Alternatively, the proximal portion 94 and distal tip portion 96 may be made from a monolithic body of material, in an embodiment.

In an alternative embodiment of the second method, the mandrel may be omitted and the sensor may be manufactured directly on the proximal portion of the tip electrode assembly, for example, or on another structure of a medical device.

Figure 7:
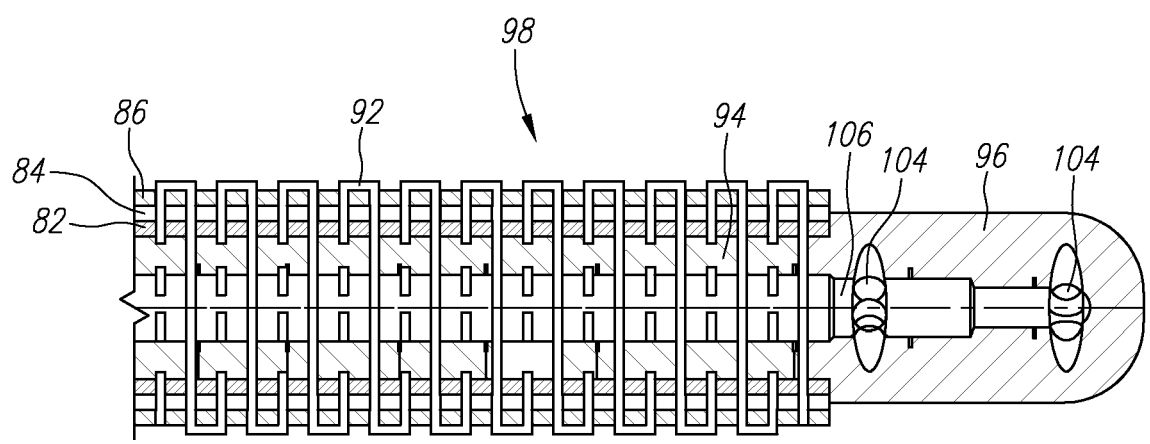
FIG. 7 is a diagrammatic cross-sectional view of a step in an alternative embodiment of the second method of integrating a sensor into a medical device structure.

FIG. 7 is a side diagrammatic view of an equivalent stage of build-up in the alternative embodiment of the second method as that illustrated in FIG. 6I. As shown in FIG. 7, in the alternative embodiment of the second method, the proximal portion 94 of the tip electrode assembly 98 and the distal tip portion 96 of the tip electrode assembly 98 may comprise a monolithic body of material. The tip electrode assembly 98 may include a longitudinal fluid lumen 106 and one or more radially-extending fluid passageways 104 extending from the longitudinal fluid lumen 106 to the exterior of the tip portion 96. Disposed about the proximal portion may be a coil 92 manufactured according to the steps illustrated in and described with respect to FIGS. 6B-6I.

FIGS. 8A-8J are diagrammatic isometric views of various steps in an exemplary embodiment of a third method of manufacturing an integrated sensor for a medical device. The third method may be executed according to CMOS fabrication techniques, in an embodiment. Accordingly, it should be understood that the deposition, masking, seeding, and other steps of the method may be the same as or similar to those used in CMOS transistor fabrication and other CMOS processes. For example, certain steps in the method may be similar to those illustrated and/or described in U.S. Pat. No. 7,262,680, which is hereby incorporated by reference.

Figure 8A:
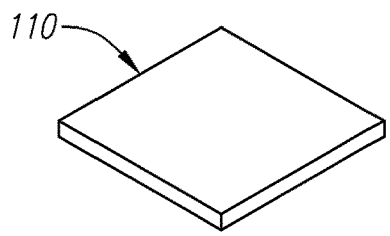
FIGS. 8A-8J are diagrammatic isometric views of various steps in a third method of integrating a sensor into a medical device structure.

Referring to FIG. 8A, the third method may begin by providing a sheet or other segment of magnetically-conductive material 110. The magnetically-conductive material 110 may be or may include mu-metal, in an exemplary embodiment.

Figure 8B:
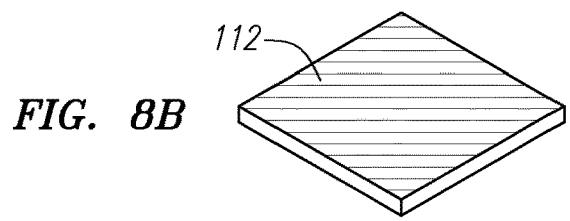

A mask layer 112 may be placed on the magnetically-conductive sheet, as shown in FIG. 8B. The mask layer 112 may be patterned, exposed, and developed to reveal a pattern 114, as illustrated in FIG. 8C. The pattern 114 may comprise a partially-annular shape, in an embodiment.

Figure 8I:
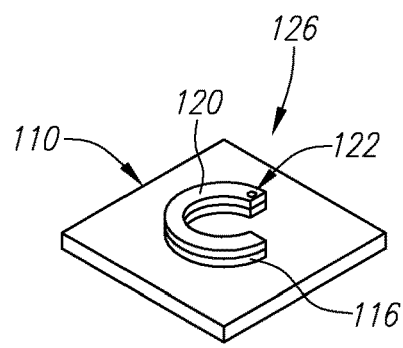
Figure 8C:
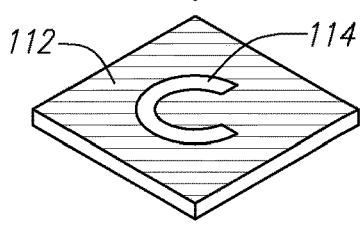
Figure 8D:
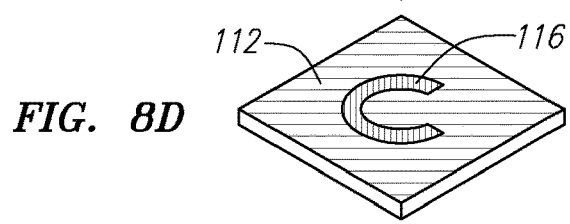
Figure 8E:
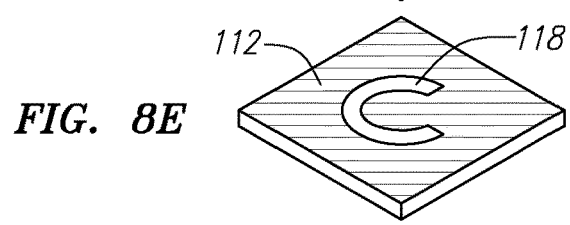
Figure 8F:
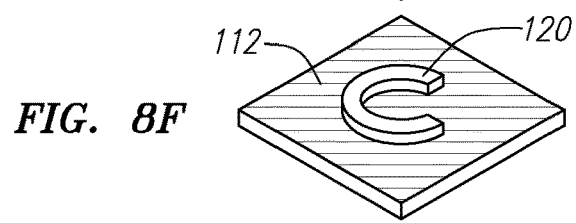

A dielectric layer 116 may be applied (e.g., deposited and patterned) to cover the non-masked portions of the magnetically-conductive material, as shown in FIG. 8D.

On the dielectric layer 116, a layer of electrically-conductive material may be applied. For example, a first electrically-conductive sub-layer 118 may be seeded, and a second electrically-conductive sub-layer 120 may be electroplated, in an embodiment, to form a unitary electrically-conductive layer 122. The electrically-conductive material may be or may include copper, in an embodiment. The dielectric layer 116 and the electrically-conductive layer 122 may both have a shape defined by the pattern 114 revealed by the mask layer 112. In an embodiment, both the dielectric layer 116 and the electrically-conductive layer 120 may include a partially-annular pattern.

Figure 8G:
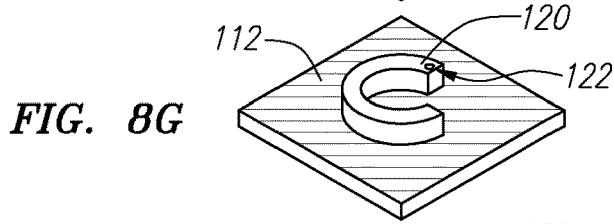
Figure 8H:
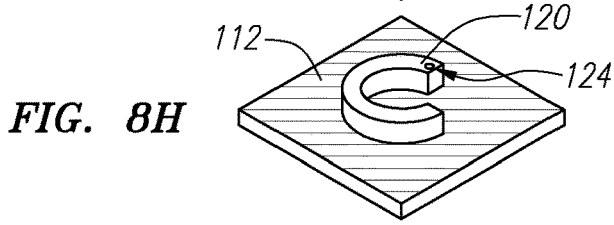

The third method may further include forming a via 122 through the electrically conductive layer 120, the dielectric layer 116, and the magnetically-conductive layer 110, and electrically coupling the via 122 with the electrically-conductive layer. Along with or instead of a via, an electrically-conductive protrusion and/or another electrical connection formation may be formed on the electrically-conductive layer. Accordingly, a process may be carried out that includes masking the electrically conductive layer and magnetically conductive layer to expose a portion of the electrically-conductive layer where the via 122 and/or protrusion are intended to be disposed, exposing the unmasked portion (i.e., exposing to relatively intense light, as known in semiconductor lithography), developing the exposed portion, and etching the via 122. The formed via 122 is shown in FIG. 8G.

The method may further include applying, such as by electroplating, an electrically-conductive material 124 in the via 122 and/or on the electrically-conductive layer to form a protrusion. The via 122 and/or the protrusion may thus be electrically coupled with the electrically-conductive layer 120. Additionally or alternatively, an electrically-conductive material may be used to fill a via, such as solder, for example only. Finally, the mask layer 112 may be stripped to again reveal the magnetically-conductive sheet 110, as shown in FIG. 8I.

The assembly of FIG. 8I, including a layer (e.g., a sheet) of magnetically-conductive material 110, a layer of dielectric material 116, a layer of electrically-conductive material 120, and a via 122 and/or protrusion, may be considered a single sensor segment 126. The steps of FIGS. 8A-8I may be repeated to create a plurality of sensor segments, in an embodiment.

Figure 8J:
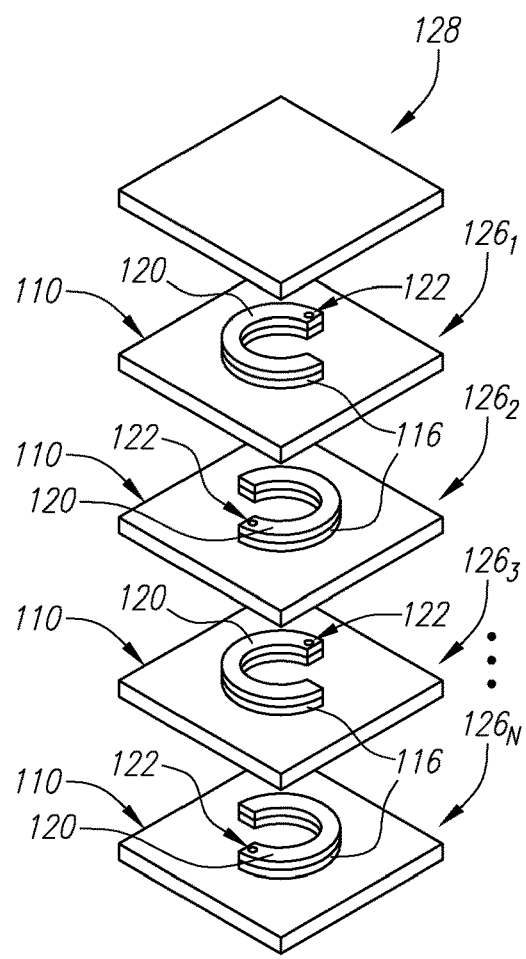

As shown in FIG. 8J, a plurality of sensor segments 126₁, 126₂, 126₃, . . . 126$_N$ may be stacked to create a multi-segment coil structure 128, in an embodiment. A via from one segment 126 may make contact with and thus be electrically coupled with an electrically-conductive protrusion from another segment, for example. Accordingly, the electrically conductive layers 120 of the plurality of sensor segments may be electrically coupled with one another and may form a continuous signal path, such as a coil. Such coupling may be effected with an electrically-conductive material, such as solder, for example only.

Figure 9:
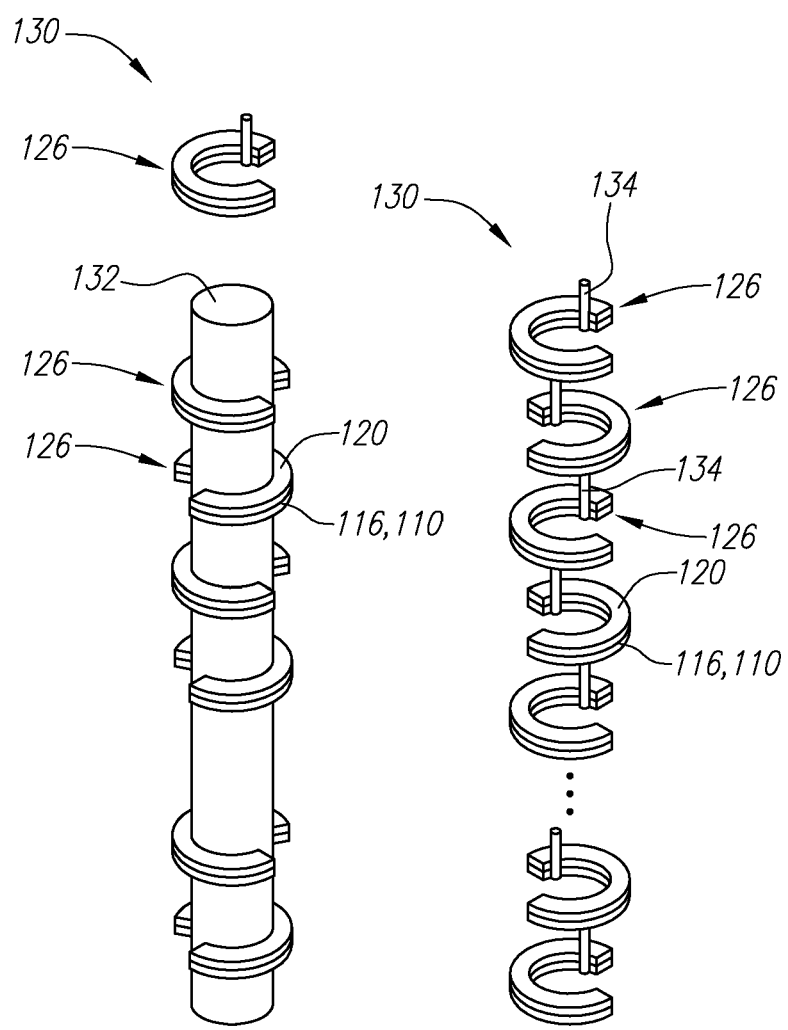
FIG. 9 is a diagrammatic isometric view of a step that may find use in an alternative embodiment of the third method of integrating a sensor into a medical device structure.

As an alternative to stacking the sensor segments including the sheets of magnetically-conductive material, portions of each sensor segment may be removed and the remaining portion of each sensor segment may be mechanically coupled with (e.g., adhered to) a common structure. FIG. 9 illustrates one such alternative coil structure 130, coupled with a core 132. In the alternative embodiment of the third method, for each sensor segment 126 (for clarity of illustration, not all such sensor segments 126 are indicated in FIG. 9), the electrically-conductive layer 120, the dielectric layer 116, and a portion of the magnetically-conductive layer 110 (e.g., the portion that shares a common pattern with the dielectric layer 116 and the electrically-conductive layer 120) may be separated from the remainder of the magnetically-conductive sheet, resulting in a plurality of singulated sensor segments 126. In FIG. 9, the magnetically-permeable layer 110 and dielectric layer 116 are shown consolidated for clarity of illustration. Also in FIG. 9, each sensor segment 126 includes a protrusion 134. The singulated sensor segments 126 may be affixed to a common structure, such as a tube 132, for example. The singulated coil segments 126 may be electrically coupled with each other through, for example and without limitation, a solder paste reflow, thermosonic bonding, etc. The singulated, electrically-coupled sensor segments 126 are illustrated in FIG. 9 both on and apart from the tube 132 for clarity of illustration. As in the first embodiment of the third method, in this alternative embodiment, the sensor segments 126 may be arranged and electrically coupled so that the electrically-conductive layers of the sensor segments form a continuous signal path, such as a coil, for example.

FIGS. 10A-10I are diagrammatic side views of various steps in an exemplary embodiment of a fourth method of manufacturing an integrated sensor for a medical device. FIGS. 11A-11H are diagrammatic top and isometric views of various steps of the fourth method.

Figure 10A:
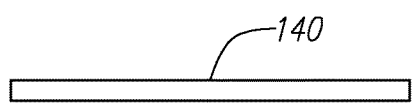
FIGS. 10A-10I are diagrammatic side views of various steps in a fourth method of integrating a sensor into a medical device structure.
Figure 11A:
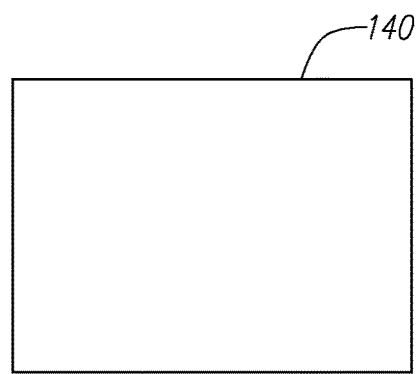
FIGS. 11A-11G are diagrammatic top and isometric views of various steps of the method of FIGS. 10A-10I.
Figure 10B:
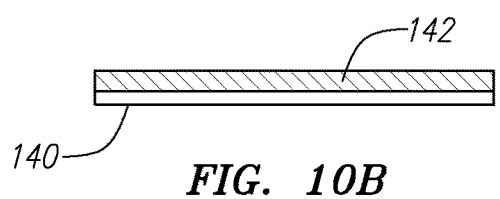

Referring to FIGS. 10A and 11A, the fourth method may begin with providing a substrate 140. The substrate 140 may be or may include a structure of a medical device, in an embodiment. The substrate 140 may be a polymer such as polyimide, in an embodiment. The substrate 140 may be a flex substrate, in an embodiment. As shown in FIG. 10B, a mask layer 142 may be placed on the substrate 140.

Figure 10C:
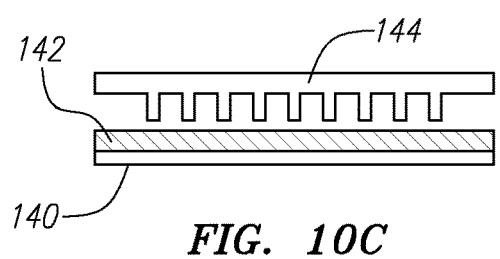
Figure 11B:
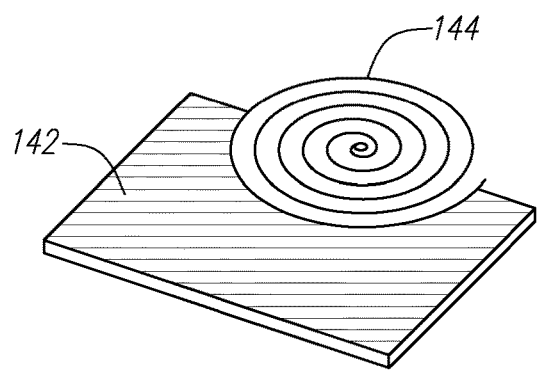

The pattern for a sensor in the fourth method may be defined by an imprinting tool 144 (e.g., a nano-imprinting tool 144). Accordingly, an imprinting tool 144 may be provided that defines a desired sensor pattern. FIGS. 10C and 11B illustrate an imprinting tool 144 disposed above the masked substrate 140. The illustrated imprinting tool 144 defines a pattern comprising a spiral. The pattern may further include rectangular or other portions intended for use as electrical contact pads in the finished sensor segment. The pattern may further include a portion intended to be removed in the final assembly for the sensor segment to be placed on another structure; for example, a circular portion may be defined in the center of the spiral, in an embodiment, for the material within the circular portion to be removed for the sensor segment to be threaded on a tube, mandrel, etc. Of course, these pattern features are exemplary in nature only and not limiting except as explicitly set forth in the claims. Instead, an imprinting tool 144 may be used to define any desired pattern, in embodiments. The imprinting tool 144 may comprise materials and construction known in the art of hereafter developed. For example, the imprinting tool 144 may comprise materials and construction described and/or illustrated in U.S. patent application publication no. 2011/0233820, which is hereby incorporated by reference.

Figure 10D:
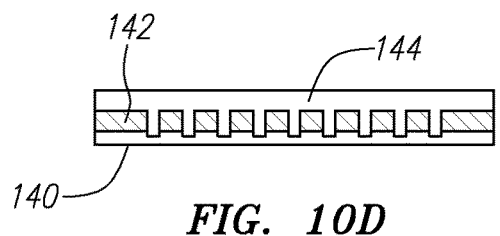
Figure 10E:
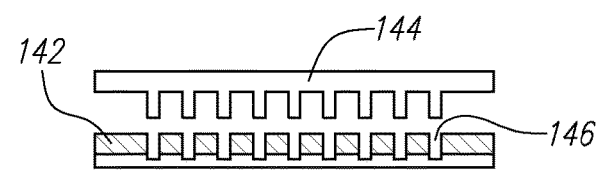
Figure 10F:
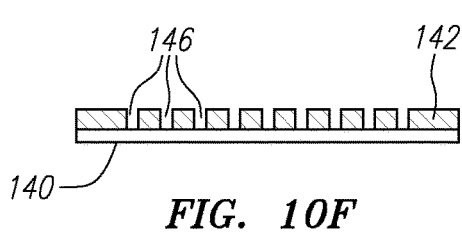
Figure 11C:
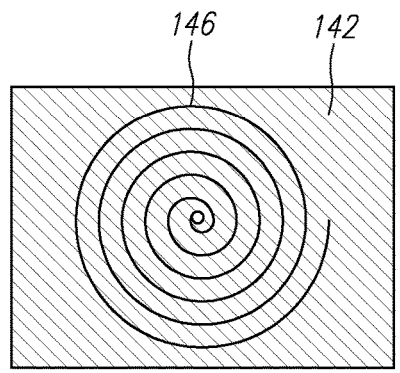

Referring to FIG. 10D, the imprinting tool 144 may be pressed into the mask layer 142 to define the pattern in the mask 142. In an embodiment, heat may be applied along with the pressure of the imprinting tool 144. The imprinting tool 144 may then be removed to leave the pattern imprinted in the mask 142 in the form of one or more channels 146, as shown in FIGS. 10E, 10F, and 11C. For example, in the illustrated embodiment, the imprinted pattern may include a continuous spiral channel. In an embodiment, a residual amount of the mask layer 142 may remain covering the channels 146 after the removal of the imprinting tool 144. In such an embodiment, the residual amount of the mask layer 142 covering the channels 146 may be etched away (e.g., dry etched).

Figure 10G:
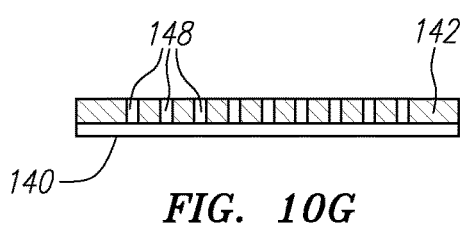

As shown in FIG. 10G, a layer of electrically-conductive material 148 may be applied to the channels 146 in the mask 142 defining the pattern (i.e., applied to the non-masked portions of the substrate 140). For example, in an embodiment, a first sub-layer of electrically-conductive material may be seeded in the non-masked portion of the substrate, and a second sub-layer of electrically-conductive material may be electroplated over the seeded layer, and the electroplated layer and seeded layer may form a single unitary layer 148 of electrically-conductive material. The electrically-conductive material 148 may be or may include copper, in an embodiment.

As an alternative to applying the imprinting tool into the mask layer 142 to define a pattern, the nano-imprinting tool may be used as a stamp. In such an embodiment, electrically-conductive material may be provided on the imprinting tool, and the imprinting tool may be pressed to the substrate 140, for example, to apply the desired pattern of electrically-conductive material.

Figure 10H:
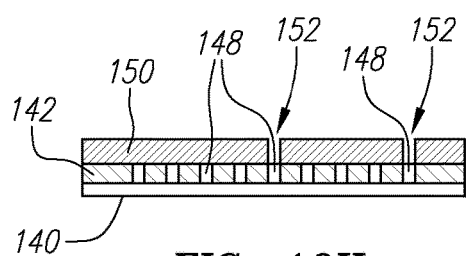
Figure 10I:
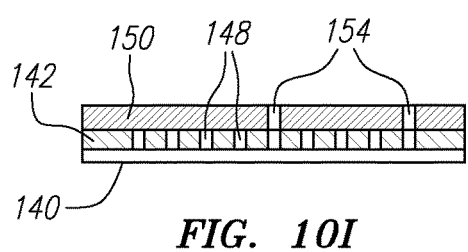
Figure 11D:
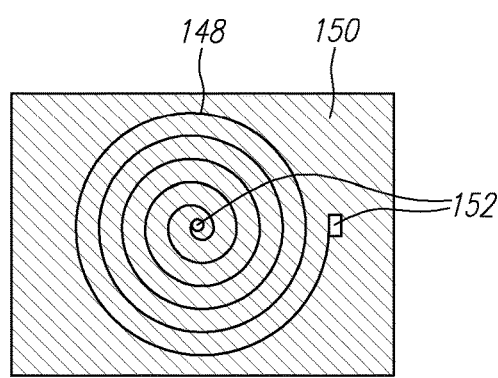

A layer of dielectric material 150 may be applied (e.g., deposited and patterned) over the electrically-conductive material 148. The result of this process is illustrated in FIGS. 10H and 11D (in FIG. 11D, the electrically-conductive material is illustrated, even though it may be obscured by the dielectric material 150 in practice). The dielectric layer 150 may be applied over all of the electrically conductive layer 148 but for one or more gaps or holes 152, in an embodiment. The gaps or holes may be for electrical connections with respective ends of the electrically-conductive layer, in an embodiment.

An electrically-conductive material 154 may be applied in the holes 152 through the dielectric layer 150. For example, an electrically conductive adhesive or solder may be applied in the holes 152. Additionally or alternatively, the holes 152 may be electroplated. Alternatively, the holes 152 may remain empty at this stage in the fourth method.

An electrically-conductive layer may also be applied on the dielectric layer 150 to provide electrical contact between the filled hole (or the electrically-conductive material 148 exposed through an unfilled hole 152) to create one or more interconnection traces 156 over the dielectric layer 150.

Figure 11E:
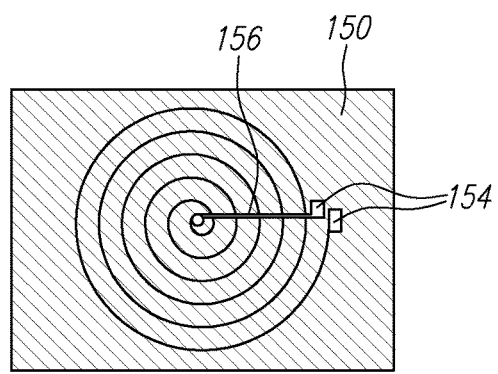

The assembly of FIG. 11E, including a substrate (not shown in FIG. 11E), dielectric layer 150, and electrically-conductive material patterned into a coil 148, contact pads 154, and traces 156, may be considered a single sensor segment 160. The steps of FIGS. 10A-10I and 11A-11F may be repeated to create a plurality of sensor segments 160, in an embodiment.

Figure 11F:
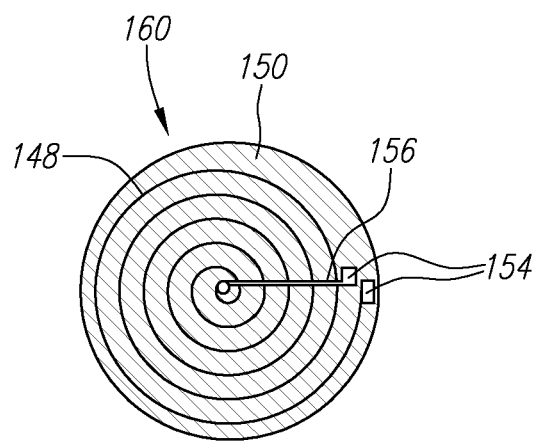

One or more sensor segments 160 may be singulated, in an embodiment. FIG. 11F illustrates a singulated sensor segment 160. One or more sensor segments 160, whether singulated or not, may find use in, for example, a position sensor, in an embodiment.

Figure 11G:
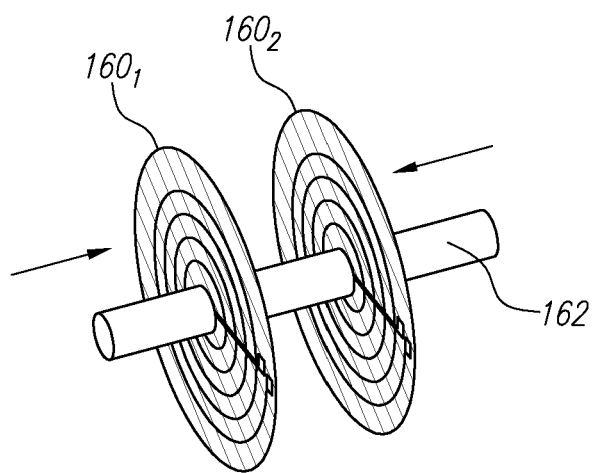

In an embodiment featuring multiple sensor segments, the multiple segments 160 may be electrically coupled with one another and/or placed on a common structure. For example, as illustrated in FIG. 11G, multiple sensor segments 160 (for example, segments $160_1$, $160_2$) may be threaded over a common core 162. The core 162 may be hollow or solid. The core 162 may be or may include a magnetically-permeable material, in an embodiment. For example, the magnetically-permeable material may be or may include mu-metal, in an embodiment.

Figure 12A:
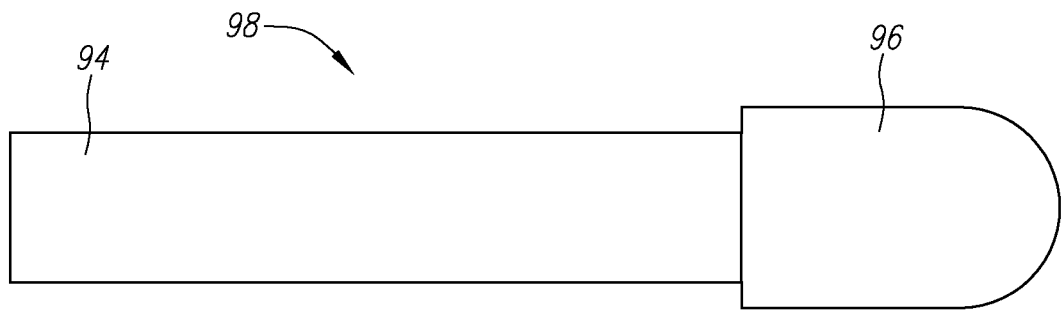
FIGS. 12A-12C are diagrammatic views of various steps of an alternative embodiment of the fourth method of integrating a sensor into a medical device structure.
Figure 12B:
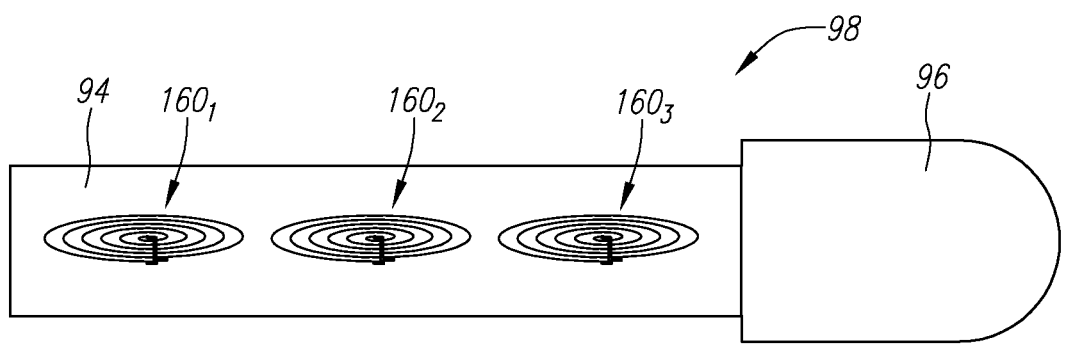
Figure 12C:
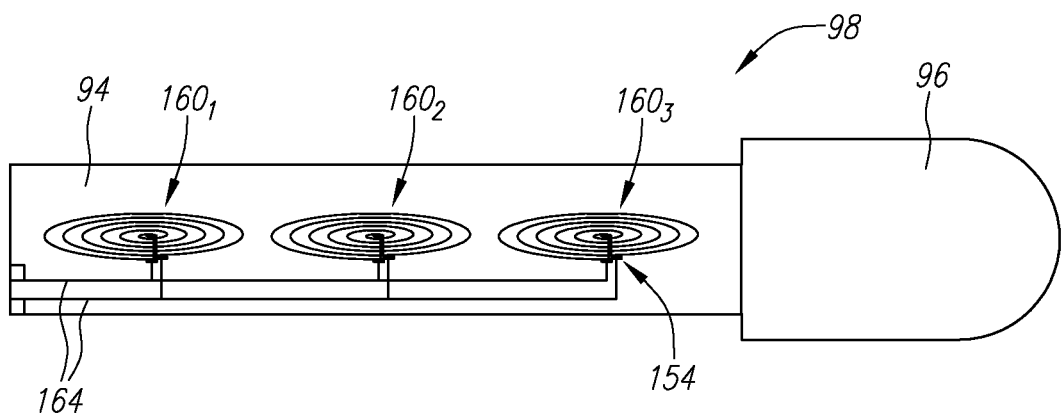

FIGS. 12A-12C are diagrammatic views of various steps of an alternative embodiment of the fourth method. In the alternative embodiment, one or more sensor segments 160 may be manufactured according to the steps set forth with respect to FIGS. 10A-10I and 11A-11G.

Referring to FIG. 12A, a tip electrode assembly 98, comprising a distal tip portion 96 and a proximal portion 94, may be provided. One or more sensor segments may be coupled with the tip electrode. For example, in an embodiment, a plurality of sensor segments 160 (three such segments $160_1$, $160_2$, $160_3$ are illustrated in FIG. 12B) may be affixed to the proximal portion 94 of the tip electrode assembly 98, as shown in FIG. 12B. A sensor segment 160 may be affixed to the tip electrode assembly 98 using an adhesive, such as a polyurethane-based adhesive or epoxy-based adhesive, in an embodiment.

In an embodiment, electrical traces 164 may also be printed on the tip electrode assembly 98, and may be electrically coupled with the contact pads 154 associated with each sensor segment 160 at one end and with other wiring at another end (e.g., for electrical coupling with another system at the proximal end of the finished medical device). For example, as illustrated in FIG. 12C, electrical traces 164 may extend from a proximal end of the proximal portion 94 of the tip electrode 98 to the contact pads 154 associated with each sensor segment 160. The electrical traces 164 may be coupled with the sensor segment contact pads 154 with solder, in an embodiment.

Numerous embodiments of methods are disclosed herein for methods of manufacturing sensors that are or can be integrated into a medical device. Those methods may be executed, for example, to manufacture coils that are or can be integrated into a medical device. Such coils may include, in embodiments, a plurality of partially-annular segments disposed around an axis, the performance of which may approximate the performance of a standard coil having similar material and size characteristics.

A particular inductance value may be required for a particular sensor application, in an embodiment. The inductance of a wound coil without a core is given by equation (1) below:

$$L = \frac{d^2 n^2}{18d + 40l} \quad (1)$$

where L=inductance (in micro Henrys (µH)), d=coil diameter (in inches (in)), n=number of turns in the coil, and l=coil length (in inches).

The inductance of a coil wound on a magnetically-permeable core is given by equation (2) below:

$$L = \frac{\pi \mu n^2 A}{250 l} \quad (2)$$

where µ=magnetic permeability of the core, n=number of turns in the coil, A=cross-sectional area of the coil, and l=coil length.

Thus, for a wound coil (with or without a magnetically-permeable core), it can be seen from equations (1) and (2) above that a desired coil inductance can be achieved through selection of an appropriate coil length, coil diameter, number of turns in the coil, and core material (if a core is used).

Referring to FIGS. 4M, 6L, 7, 8J, and 9, coils having partially-annular segments manufactured according to the present disclosure may be designed for a desired inductance through selection of similar parameters to those selected for a wound coil. That is, the number of "turns," the diameter of the coil, and the length of the electrically-conductive trace forming the coil may be selected to achieve a desired inductance for a coil integrated into a medical device.

For a planar spiral coil, the inductance is given by equation (3) below:

$$L = \frac{n^2 r^2}{8r + 11c} \quad (3)$$

where L=inductance, n=number of turns, r=mean radius of the turns, and c=thickness of the coil on one radial side (i.e., between the inner diameter of the coil and the outer diameter of the coil).

Referring to FIG. 11G, the inductance of the spiral coil formed by the patterned electrically-conductive layer may be calculated according to equation (3). Accordingly, to achieve a desired inductance for a coil, the number of windings, mean radius, and thickness of the coil may be selected. Additionally or alternatively, multiple coils (i.e., multiple sensor segments) may be provided and connected in parallel (as shown in FIG. 12C) to increase the inductance of the sensor.

Figure 13A:
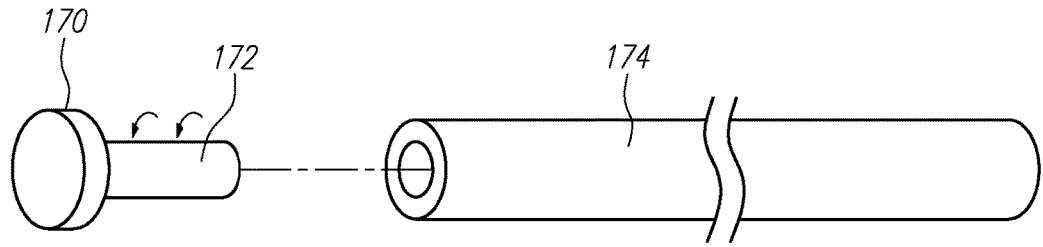
FIGS. 13A-13J are diagrammatic views illustrating a fifth exemplary embodiment of a method of manufacturing a medical device sensor.

FIGS. 13A-13J are diagrammatic views illustrating a fifth exemplary embodiment of a method of manufacturing a medical device sensor. The method may generally involve printing or otherwise applying the sensor directly on a tubular surface. In an embodiment, as shown in FIG. 13A, the method may begin with a step that includes providing a rotating fixture 170 coupled with a mandrel 172 and also providing a tubular substrate 174. The rotating fixture 170 may comprise a stepper motor, servo motor, and/or other appropriate device. The mandrel 172 may be coupled with the rotating fixture 170 so that the rotating fixture 170 provides rotation to the mandrel 172. The tubular substrate 174 may be made of or may include a polymer, such as an extruded thermoplastic, a thermoplastic elastomer, or a solution-case polymer, in an embodiment. For example, the tubular substrate 174 may be or may include polyimide.

Figure 13B:
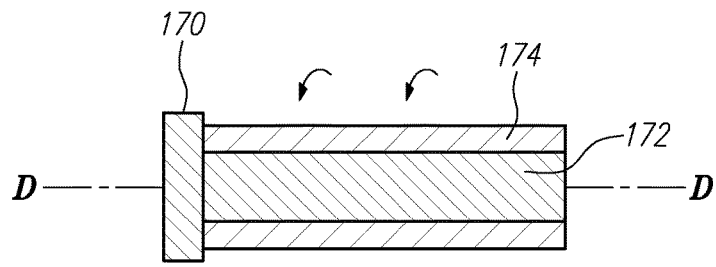

FIG. 13B illustrates a further step in the method, which may include placing the tubular substrate 174 on the mandrel 172. The substrate 172 may define a longitudinal axis D. The substrate 174 may be disposed so that the mandrel 172 is radially-inward of the substrate 174. The mandrel 172 may also be radially symmetric about the longitudinal axis D of the substrate. The rotating fixture 170 may be configured to rotate the mandrel 172 (and, thus, the substrate 174) about the longitudinal axis D of the substrate 174. Thus, the rotational axis of the mandrel 172 may coincide with the longitudinal axis D of the substrate 174.

Figure 13C:
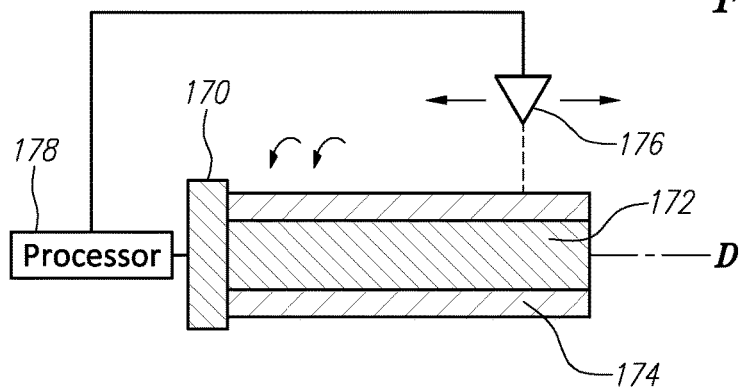
Figure 13D:
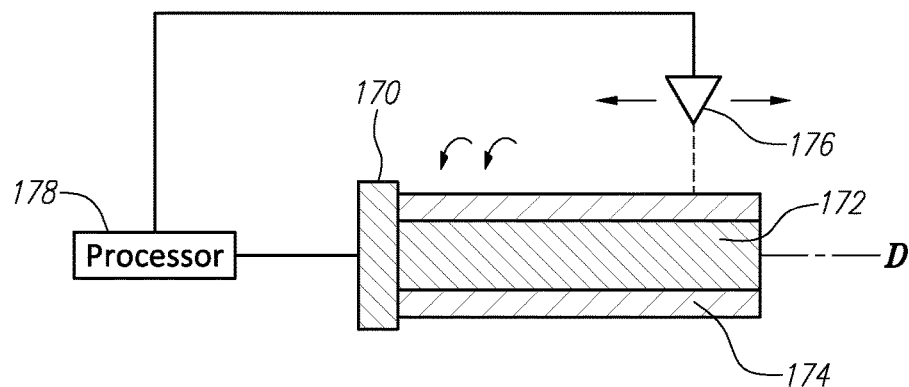

Referring to FIGS. 13C and 13D, the method may further include a step that includes providing a printer radially-outward from the tubular substrate 174. The printer may comprise a print head 176 that is configured to move parallel to the longitudinal axis D of the substrate 174. The printer may be an ink jet printer, an aerosol ink jet printer, an electric field assist aerosol jet printer, or another appropriate type of printing device.

The printer (i.e., the print head 176) and the rotating fixture 170 may be in electrical communication with a processing device 178 configured to control the rotating fixture 170 and the print head 176 to print layers of material to, e.g., create one or more sensors. Thus, the processing device 178 may be configured to execute one or more of the steps of the fifth method.

For example, in an embodiment, the processing device may be configured to execute a preprogrammed set of instructions to rotate the mandrel 172 (i.e., by controlling the rotating fixture 170) and control the movement and release of ink material from the print head 176 to create one or more layers of material on the substrate 174, such as one or more layers of electrically-conductive material to form one or more sensors.

In an embodiment, printing may include stepping through longitudinal positions—printing all radial elements of a desired pattern at a given longitudinal position (i.e., by rotating the fixture 170 and releasing ink as the fixture 170 rotates with the print head 176 held in a static position), then moving the print head 176 to the next longitudinal position, printing all radial elements of the pattern at that longitudinal position, and so on. For example, all elements of a pattern may be printed at the longitudinal position of the print head 176 illustrated in FIG. 13C, then all element of the pattern may be printed at the longitudinal position illustrated in 13D, and so on.

In an alternate embodiment, printing may include stepping through radial positions—printing all longitudinal elements of a desired pattern at a given radial position (i.e., by translating the print head 176 and releasing ink with the fixture 170 held in a static rotational position), then moving the fixture 170 to the next rotational position, printing all longitudinal elements of the pattern at that rotational position, and so on.

Still further, in an embodiment, printing may include simultaneous rotation of the fixture 170 and longitudinal movement of the print head 176.

The processing device 178 may control the print head 176 and rotating fixture 170 in a cylindrical coordinate frame, in an embodiment. Accordingly, the processing device 178 may be configured to relate coordinates of a pattern in a Cartesian coordinate frame (X, Y, Z) into a rotational coordinate frame (r, θ, Z) as set forth in equations (4) and (5) below (where Z in the rotational coordinate frame is the same as Z in the Cartesian coordinate frame):

$$x = r \cos \theta \quad (4)$$

$$y = r \sin \theta \quad (5)$$

Figure 13E:
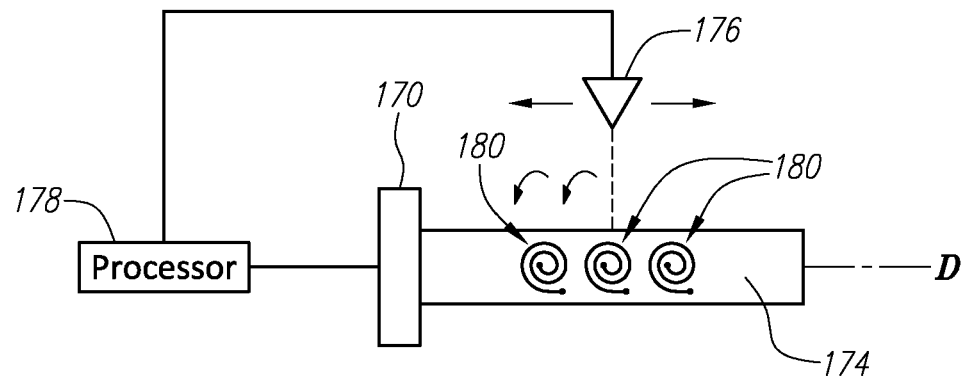

As shown in FIG. 13E, the method may further include controlling the rotating fixture 170 and the print head 176 to print one or more spiral patterns 180 of electrically-conductive material on the substrate 174. Additionally or alternatively, the rotating fixture 170 and the print head 176 may be controlled to print one or more other sensor patterns on the substrate 174. An embodiment including only spiral patterns will be described for the remainder of the fifth method, but the fifth method is not limited to spiral patterns except as expressly set forth in the claims.

Figure 13F:
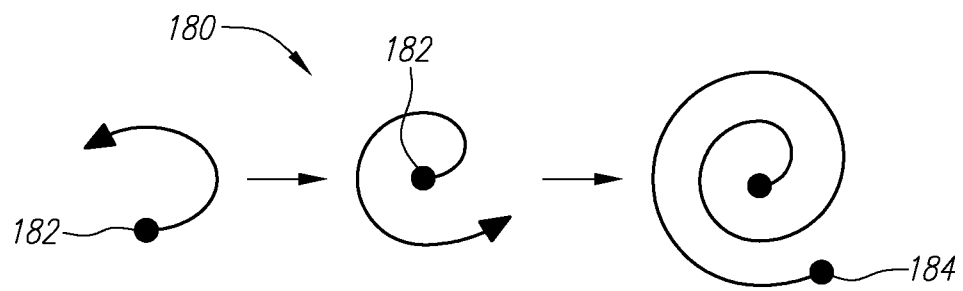

As shown in FIG. 13F, printing a spiral pattern 180 may include printing from the center point 182 of the spiral, moving outwards to the end 184 of the spiral. Alternatively, a spiral pattern 180 may be printed according to a process involving stepping through longitudinal or radial positions, as described above. In any event, a spiral pattern may be printed such that electrical current flows through the spiral along the spiral pattern (i.e., with the "center" 182 of the spiral as a first electrical terminal, and the "end" 184 of the spiral as a second electrical terminal).

The method may further include steps for printing electrically-conductive traces (or otherwise applying such traces) to connect the spiral patterns 180 in series, in an embodiment. For example, the "center" points 182 of the spirals may be connected in a first series, and the "end" points 184 of the spirals may be connected in a second series, with the first and second series electrically isolated from each other. Further steps in the fifth method may result in such series connections.

Figure 13G:
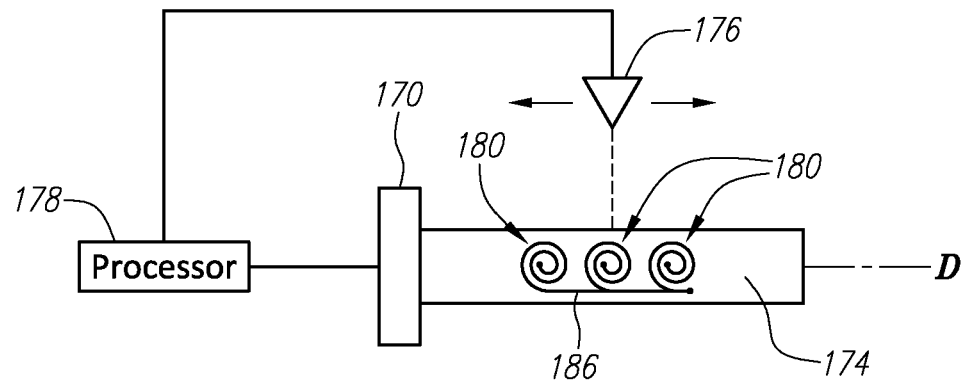

Referring to FIG. 13G, the method may include a step that includes printing a first electrically-conductive pattern 186 to connect the "ends" of the spirals in series. The series connection may be printed on the substrate 174 (i.e., in the same radial layer as the spiral patterns), on the embodiment. Alternatively, the series connection may be electroplated or otherwise applied, in an embodiment.

Figure 13H:
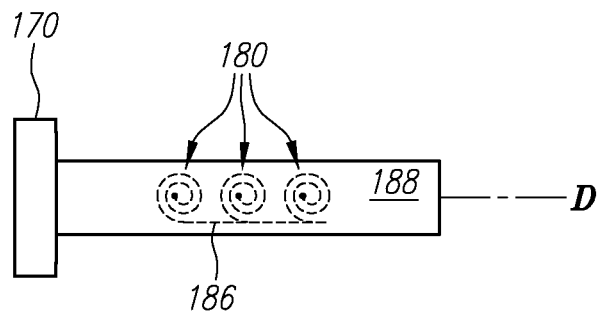

With reference to FIG. 13H, the method may further include a step that includes applying a layer of dielectric material 188 over the electrically-conductive sensor patterns 180 (though covered, the sensor patterns 180 and trace pattern 186 are illustrated in phantom). In an embodiment, the dielectric material 188 may be applied over the entirety of the exposed portions of the substrate 174 and the electrically-conductive material 180, 186.

The dielectric material layer 188 may be applied according to a Parylene vapor deposition procedure, in an embodiment. In such a procedure, the cylindrical substrate 174 may be suspended via fixturing, in which a mandrel is placed within the inside diameter of (i.e. a lumen formed by) the substrate 174. The suspended substrate 174 may be placed within a deposition chamber, enabling circumferential dielectric deposition. Alternative methods of applying the dielectric material 188 may include spray coating or dip coating dielectric materials such as SU-8 3000 from Kayaku Microchem, Enthone USR-7, or Taiyo PSR 4000 series materials. Spray coating may employ a rotational fixture (similar to that described hereinabove), in which the substrate 174 is suspended and rotated while being spray-coated. Dip coating process may include dipping the substrate 174 (and any materials disposed in the substrate) into dielectric material 188 and then removed at a controlled rate, allowing gravity to cause the coating solution to flow from the substrate surface. Such polymer solution casting processes are described by Avalon Laboratories, Rancho Dominguez, Calif.

Figure 13I:
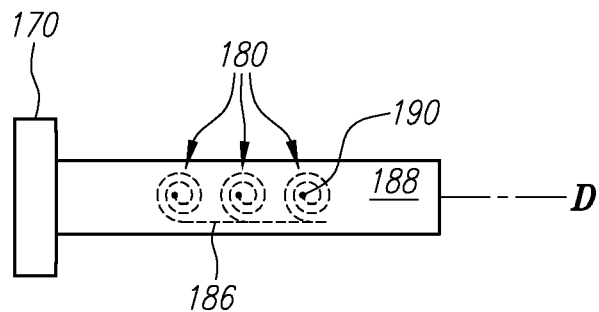

As shown in FIG. 13I, the method may further include a step that includes forming holes 190 in the dielectric layer above the "centers" of the spiral 180 (only one such hole 190 is indicated in FIG. 13I for clarity of illustration, though three holes are illustrated). Forming such holes 190 may include, for example, a pattern, develop, and strip process as described previously in this disclosure.

With continued reference to FIG. 13I, the method may further include a step that includes coating or filling the holes 190 with an electrically-conductive material to form electrically-conductive vias, in an embodiment. The electrically-conductive material may be printed, electroplated, or otherwise applied, in an embodiment.

Figure 13J:
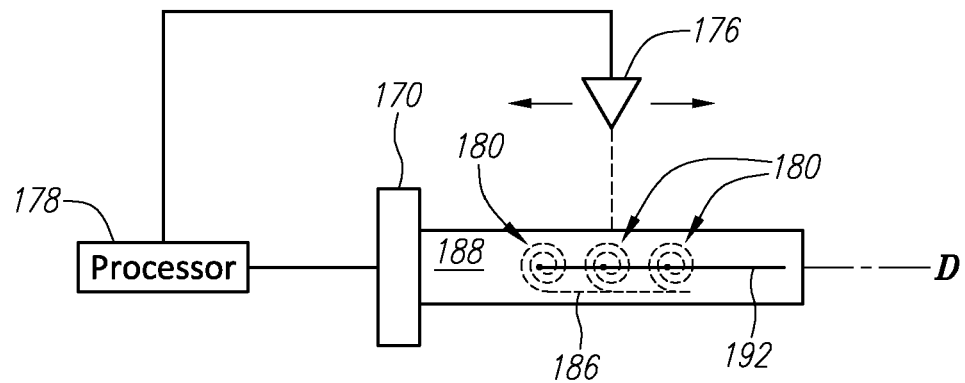

Referring to FIG. 13J, the method may further include a step that includes applying a layer of electrically-conductive material 192 (e.g., traces) to form the series connection for the spiral centers, in an embodiment. The electrically-conductive series connection 192 may be applied by printing, electroplating, or some other application technique, in embodiments.

Although numerous embodiments of this invention have been described above with a certain degree of particularity, those skilled in the art could make numerous alterations to the disclosed embodiments without departing from the spirit or scope of this disclosure. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the any aspect of the disclosure. As used herein, the phrased "configured to," "configured for," and similar phrases indicate that the subject device, apparatus, or system is designed and/or constructed (e.g., through appropriate hardware, software, and/or components) to fulfill one or more specific object purposes, not that the subject device, apparatus, or system is merely capable of performing the object purpose. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A sensor for a medical device, the sensor comprising:
a plurality of sensor segments, each one of said plurality of sensor segments comprising:
   a layer of magnetically-permeable material;
   a layer of electrically-conductive material disposed on the layer of magnetically-permeable material in a partially-annular shape; and
   an electrical connection formation that extends transverse to the layers of magnetically-permeable material and electrically-conductive material, wherein the electrical connection formation is electrically coupled with the layer of electrically-conductive material;
wherein the plurality of sensor segments are electrically coupled with each other through an electrical coupling of the respective layer of electrically-conductive material of each sensor segment with the electrical connection formation of another sensor segment.

2. The sensor of claim 1, wherein the electrical connection formation of at least one of the sensor segments comprises a via.

3. The sensor of claim 1, wherein the electrical connection formation of at least one of the sensor segments comprises a protrusion.

4. The sensor of claim 1, wherein each one of said plurality of sensor layers is singulated from a sheet of magnetically-permeable material.

5. The sensor of claim 4, wherein the sensor layers are stacked so that the partially-annular shapes define a longitudinal axis, wherein each of the partially-annular shapes is disposed around the longitudinal axis.

6. The sensor of claim 5, wherein the electrically-conductive layers of the plurality of sensor segments are electrically coupled with one another and may form a continuous signal path.

7. The sensor of claim 6, wherein the electrically-conductive layers of the plurality of sensor segments form a continuous signal path arranged as a coil.

8. The sensor of claim 1, wherein the coupling is solder.

9. The sensor of claim 1, wherein the coupling is thermosonic bonding.

10. The sensor of claim 1, wherein a portion of each sensor segment may be mechanically coupled to a common structure.

11. The sensor of claim 10, wherein the common structure includes a medical device.

12. The sensor of claim 10, wherein the plurality of segments are threaded over the common structure.

13. The sensor of claim 10, wherein the common structure is a magnetically permeable structure.

14. The sensor of claim 1, further comprising a substrate, wherein the layer of magnetically-permeable material is disposed on the substrate.

15. The sensor of claim 14, wherein the substrate includes a polymer.

16. The sensor of claim 14, wherein the substrate includes a flex substrate.

17. The sensor of claim 14, further comprising a mask layer disposed on the substrate, wherein the layer of electrically-conductive material is deposited in a channel of the mask layer.

18. The sensor of claim 17, wherein a layer of dielectric material is disposed over the mask layer.

19. The sensor of claim 1, wherein the electrically-conductive material of one or more of the plurality of sensor segments is electrically coupled with the tip electrode.

* * * * *